US012774325B2

(12) United States Patent
Fu et al.

(10) Patent No.: US 12,774,325 B2
(45) Date of Patent: Oct. 27, 2026

(54) ANTI-ANGIOPOIETIN-LIKE PROTEIN 3 (ANGPTL3) ANTIBODY AND PHARMACEUTICAL COMPOSITION THEREOF

(71) Applicant: JIANGSU HENGRUI PHARMACEUTICALS CO., LTD., Lianyungang (CN)

(72) Inventors: Yayuan Fu, Shanghai (CN); Yingxia Xu, Shanghai (CN); Bing Lin, Shanghai (CN); Weikang Tao, Shanghai (CN)

(73) Assignee: JIANGSU HENGRUI PHARMACEUTICALS CO., LTD., Lianyungang (CN)

( * ) Notice: Subject to any disclaimer, the term of this patent is extended or adjusted under 35 U.S.C. 154(b) by 216 days.

(21) Appl. No.: 17/794,213

(22) PCT Filed: Jan. 22, 2021

(86) PCT No.: PCT/CN2021/073239

§ 371 (c)(1),
(2) Date: Jul. 20, 2022

(87) PCT Pub. No.: WO2021/147984

PCT Pub. Date: Jul. 29, 2021

(65) Prior Publication Data

US 2023/0138315 A1 May 4, 2023

(30) Foreign Application Priority Data

Jan. 22, 2020 (CN) ......................... 202010073192.4

(51) Int. Cl.
*A61K 39/395* (2006.01)
*A61P 3/06* (2006.01)
*C07K 16/22* (2006.01)

(52) U.S. Cl.
CPC ................ *C07K 16/22* (2013.01); *A61P 3/06* (2018.01); *C07K 2317/565* (2013.01)

(58) Field of Classification Search
None
See application file for complete search history.

(56) References Cited

FOREIGN PATENT DOCUMENTS

| | | | | |
|---|---|---|---|---|
| CN | 101855241 A | | 10/2010 | |
| CN | 103732624 A | | 4/2014 | |
| CN | 107085112 A | | 8/2017 | |
| CN | 108697797 A | | 10/2018 | |
| CN | 109789194 A | | 5/2019 | |
| WO | 2008073300 A2 | | 6/2008 | |
| WO | WO-2012174178 A1 | * | 12/2012 | ................ A61P 9/00 |

OTHER PUBLICATIONS

Gieri Camenisch et al., ANGPTL3 Stimulates Endothelial Cell Adhesion and Migration via Integrin αvβ3 and Induces Blood Vessel Formation in Vivo, The Journal of Biological Chemistry, May 2002, vol. 277, No. 19, pp. 17281-17290, U.S. (10 pages).
Yan Wang et al., Inactivation of ANGPTL3 reduces hepatic VLDL-triglyceride secretion 1, Journal of Lipid Research, 2015, vol. 56, pp. 1296-1307, U.S. (12 pages).
Conklin D., et al., "Identification of a mammalian angiopoietin-related protein expressed specifically in liver." Genomics. Dec. 15, 1999;62(3):477-82.

* cited by examiner

*Primary Examiner* — Christine J Saoud
(74) *Attorney, Agent, or Firm* — Morgan, Lewis & Bockius LLP

(57) ABSTRACT

The present invention relates to an anti-angiopoietin-like protein 3(ANGPTL3) antibody and a use thereof. In particular, the present invention relates to the anti-ANGPTL3 antibody and an antigen-binding fragment thereof, or a pharmaceutically acceptable salt or solvent thereof, and a use thereof as a medicine, in particular a use in the preparation of a medicine for treating hyperlipidemia.

13 Claims, 5 Drawing Sheets

Specification includes a Sequence Listing.

SEQUENCE LISTING

```
<160> NUMBER OF SEQ ID NOS: 36

<210> SEQ ID NO 1
<211> LENGTH: 473
<212> TYPE: PRT
<213> ORGANISM: Artificial Sequence
<220> FEATURE:
<223> OTHER INFORMATION: Synthetic Sequence_Human ANGPTL3(17-460)-His
      sequence

<400> SEQUENCE: 1

Met Glu Phe Gly Leu Ser Trp Leu Phe Leu Val Ala Ile Leu Lys Gly
1               5                   10                  15

Val Gln Cys Ser Arg Ile Asp Gln Asp Asn Ser Ser Phe Asp Ser Leu
            20                  25                  30
```

```
Ser Pro Glu Pro Lys Ser Arg Phe Ala Met Leu Asp Asp Val Lys Ile
        35                  40                  45

Leu Ala Asn Gly Leu Leu Gln Leu Gly His Gly Leu Lys Asp Phe Val
    50                  55                  60

His Lys Thr Lys Gly Gln Ile Asn Asp Ile Phe Gln Lys Leu Asn Ile
65                  70                  75                  80

Phe Asp Gln Ser Phe Tyr Asp Leu Ser Leu Gln Thr Ser Glu Ile Lys
                85                  90                  95

Glu Glu Glu Lys Glu Leu Arg Arg Thr Thr Tyr Lys Leu Gln Val Lys
            100                 105                 110

Asn Glu Glu Val Lys Asn Met Ser Leu Glu Leu Asn Ser Lys Leu Glu
        115                 120                 125

Ser Leu Leu Glu Glu Lys Ile Leu Leu Gln Gln Lys Val Lys Tyr Leu
    130                 135                 140

Glu Glu Gln Leu Thr Asn Leu Ile Gln Asn Gln Pro Glu Thr Pro Glu
145                 150                 155                 160

His Pro Glu Val Thr Ser Leu Lys Thr Phe Val Glu Lys Gln Asp Asn
                165                 170                 175

Ser Ile Lys Asp Leu Leu Gln Thr Val Glu Asp Gln Tyr Lys Gln Leu
            180                 185                 190

Asn Gln Gln His Ser Gln Ile Lys Glu Ile Glu Asn Gln Leu Arg Arg
        195                 200                 205

Thr Ser Ile Gln Glu Pro Thr Glu Ile Ser Leu Ser Ser Lys Pro Arg
    210                 215                 220

Ala Pro Arg Thr Thr Pro Phe Leu Gln Leu Asn Glu Ile Arg Asn Val
225                 230                 235                 240

Lys His Asp Gly Ile Pro Ala Glu Cys Thr Thr Ile Tyr Asn Arg Gly
                245                 250                 255

Glu His Thr Ser Gly Met Tyr Ala Ile Arg Pro Ser Asn Ser Gln Val
            260                 265                 270

Phe His Val Tyr Cys Asp Val Ile Ser Gly Ser Pro Trp Thr Leu Ile
        275                 280                 285

Gln His Arg Ile Asp Gly Ser Gln Asn Phe Asn Glu Thr Trp Glu Asn
    290                 295                 300

Tyr Lys Tyr Gly Phe Gly Arg Leu Asp Gly Glu Phe Trp Leu Gly Leu
305                 310                 315                 320

Glu Lys Ile Tyr Ser Ile Val Lys Gln Ser Asn Tyr Val Leu Arg Ile
                325                 330                 335

Glu Leu Glu Asp Trp Lys Asp Asn Lys His Tyr Ile Glu Tyr Ser Phe
            340                 345                 350

Tyr Leu Gly Asn His Glu Thr Asn Tyr Thr Leu His Leu Val Ala Ile
        355                 360                 365

Thr Gly Asn Val Pro Asn Ala Ile Pro Glu Asn Lys Asp Leu Val Phe
    370                 375                 380

Ser Thr Trp Asp His Lys Ala Lys Gly His Phe Asn Cys Pro Glu Gly
385                 390                 395                 400

Tyr Ser Gly Gly Trp Trp Trp His Asp Glu Cys Gly Glu Asn Asn Leu
                405                 410                 415

Asn Gly Lys Tyr Asn Lys Pro Arg Ala Lys Ser Lys Pro Glu Arg Arg
            420                 425                 430

Arg Gly Leu Ser Trp Lys Ser Gln Asn Gly Arg Leu Tyr Ser Ile Lys
        435                 440                 445

Ser Thr Lys Met Leu Ile His Pro Thr Asp Ser Glu Ser Phe Glu His
```

```
    450                 455                 460

His His His His His His His His His
465                 470


<210> SEQ ID NO 2
<211> LENGTH: 190
<212> TYPE: PRT
<213> ORGANISM: Artificial Sequence
<220> FEATURE:
<223> OTHER INFORMATION: Synthetic Sequence_Human ANGPTL3(17-170)-Flag-
      His sequence

<400> SEQUENCE: 2

Met Glu Phe Gly Leu Ser Trp Leu Phe Leu Val Ala Ile Leu Lys Gly
1               5                   10                  15

Val Gln Cys Ser Arg Ile Asp Gln Asp Asn Ser Ser Phe Asp Ser Leu
            20                  25                  30

Ser Pro Glu Pro Lys Ser Arg Phe Ala Met Leu Asp Asp Val Lys Ile
        35                  40                  45

Leu Ala Asn Gly Leu Leu Gln Leu Gly His Gly Leu Lys Asp Phe Val
    50                  55                  60

His Lys Thr Lys Gly Gln Ile Asn Asp Ile Phe Gln Lys Leu Asn Ile
65                  70                  75                  80

Phe Asp Gln Ser Phe Tyr Asp Leu Ser Leu Gln Thr Ser Glu Ile Lys
                85                  90                  95

Glu Glu Glu Lys Glu Leu Arg Arg Thr Thr Tyr Lys Leu Gln Val Lys
            100                 105                 110

Asn Glu Glu Val Lys Asn Met Ser Leu Glu Leu Asn Ser Lys Leu Glu
        115                 120                 125

Ser Leu Leu Glu Glu Lys Ile Leu Leu Gln Gln Lys Val Lys Tyr Leu
    130                 135                 140

Glu Glu Gln Leu Thr Asn Leu Ile Gln Asn Gln Pro Glu Thr Pro Glu
145                 150                 155                 160

His Pro Glu Val Thr Ser Leu Lys Thr Phe Val Glu Lys Gly Ser Ser
                165                 170                 175

Asp Tyr Lys Asp Asp Asp Asp Lys His His His His His His
            180                 185                 190


<210> SEQ ID NO 3
<211> LENGTH: 406
<212> TYPE: PRT
<213> ORGANISM: Artificial Sequence
<220> FEATURE:
<223> OTHER INFORMATION: Synthetic Sequence_Human ANGPTL3(17-170)-mFc
      sequence

<400> SEQUENCE: 3

Met Glu Phe Gly Leu Ser Trp Leu Phe Leu Val Ala Ile Leu Lys Gly
1               5                   10                  15

Val Gln Cys Ser Arg Ile Asp Gln Asp Asn Ser Ser Phe Asp Ser Leu
            20                  25                  30

Ser Pro Glu Pro Lys Ser Arg Phe Ala Met Leu Asp Asp Val Lys Ile
        35                  40                  45

Leu Ala Asn Gly Leu Leu Gln Leu Gly His Gly Leu Lys Asp Phe Val
    50                  55                  60

His Lys Thr Lys Gly Gln Ile Asn Asp Ile Phe Gln Lys Leu Asn Ile
65                  70                  75                  80

Phe Asp Gln Ser Phe Tyr Asp Leu Ser Leu Gln Thr Ser Glu Ile Lys
```

```
                85                  90                  95

Glu Glu Glu Lys Glu Leu Arg Arg Thr Thr Tyr Lys Leu Gln Val Lys
            100                 105                 110

Asn Glu Glu Val Lys Asn Met Ser Leu Glu Leu Asn Ser Lys Leu Glu
        115                 120                 125

Ser Leu Leu Glu Glu Lys Ile Leu Leu Gln Gln Lys Val Lys Tyr Leu
    130                 135                 140

Glu Glu Gln Leu Thr Asn Leu Ile Gln Asn Gln Pro Glu Thr Pro Glu
145                 150                 155                 160

His Pro Glu Val Thr Ser Leu Lys Thr Phe Val Glu Lys Glu Pro Arg
                165                 170                 175

Gly Pro Thr Ile Lys Pro Cys Pro Pro Cys Lys Cys Pro Ala Pro Asn
            180                 185                 190

Leu Leu Gly Gly Pro Ser Val Phe Ile Phe Pro Pro Lys Ile Lys Asp
        195                 200                 205

Val Leu Met Ile Ser Leu Ser Pro Ile Val Thr Cys Val Val Val Asp
    210                 215                 220

Val Ser Glu Asp Asp Pro Asp Val Gln Ile Ser Trp Phe Val Asn Asn
225                 230                 235                 240

Val Glu Val His Thr Ala Gln Thr Gln Thr His Arg Glu Asp Tyr Asn
                245                 250                 255

Ser Thr Leu Arg Val Val Ser Ala Leu Pro Ile Gln His Gln Asp Trp
            260                 265                 270

Met Ser Gly Lys Glu Phe Lys Cys Lys Val Asn Asn Lys Asp Leu Pro
        275                 280                 285

Ala Pro Ile Glu Arg Thr Ile Ser Lys Pro Lys Gly Ser Val Arg Ala
    290                 295                 300

Pro Gln Val Tyr Val Leu Pro Pro Pro Glu Glu Glu Met Thr Lys Lys
305                 310                 315                 320

Gln Val Thr Leu Thr Cys Met Val Thr Asp Phe Met Pro Glu Asp Ile
                325                 330                 335

Tyr Val Glu Trp Thr Asn Asn Gly Lys Thr Glu Leu Asn Tyr Lys Asn
            340                 345                 350

Thr Glu Pro Val Leu Asp Ser Asp Gly Ser Tyr Phe Met Tyr Ser Lys
        355                 360                 365

Leu Arg Val Glu Lys Lys Asn Trp Val Glu Arg Asn Ser Tyr Ser Cys
    370                 375                 380

Ser Val Val His Glu Gly Leu His Asn His His Thr Thr Lys Ser Phe
385                 390                 395                 400

Ser Arg Thr Pro Gly Lys
                405


<210> SEQ ID NO 4
<211> LENGTH: 456
<212> TYPE: PRT
<213> ORGANISM: Artificial Sequence
<220> FEATURE:
<223> OTHER INFORMATION: Synthetic Sequence_Human ANGPTL3(17-220)-mFc
      sequence

<400> SEQUENCE: 4

Met Glu Phe Gly Leu Ser Trp Leu Phe Leu Val Ala Ile Leu Lys Gly
1               5                   10                  15

Val Gln Cys Ser Arg Ile Asp Gln Asp Asn Ser Ser Phe Asp Ser Leu
            20                  25                  30
```

```
Ser Pro Glu Pro Lys Ser Arg Phe Ala Met Leu Asp Asp Val Lys Ile
        35                  40                  45

Leu Ala Asn Gly Leu Leu Gln Leu Gly His Gly Leu Lys Asp Phe Val
    50                  55                  60

His Lys Thr Lys Gly Gln Ile Asn Asp Ile Phe Gln Lys Leu Asn Ile
65                  70                  75                  80

Phe Asp Gln Ser Phe Tyr Asp Leu Ser Leu Gln Thr Ser Glu Ile Lys
                85                  90                  95

Glu Glu Glu Lys Glu Leu Arg Arg Thr Thr Tyr Lys Leu Gln Val Lys
            100                 105                 110

Asn Glu Glu Val Lys Asn Met Ser Leu Glu Leu Asn Ser Lys Leu Glu
        115                 120                 125

Ser Leu Leu Glu Glu Lys Ile Leu Leu Gln Gln Lys Val Lys Tyr Leu
    130                 135                 140

Glu Glu Gln Leu Thr Asn Leu Ile Gln Asn Gln Pro Glu Thr Pro Glu
145                 150                 155                 160

His Pro Glu Val Thr Ser Leu Lys Thr Phe Val Glu Lys Gln Asp Asn
                165                 170                 175

Ser Ile Lys Asp Leu Leu Gln Thr Val Glu Asp Gln Tyr Lys Gln Leu
            180                 185                 190

Asn Gln Gln His Ser Gln Ile Lys Glu Ile Glu Asn Gln Leu Arg Arg
        195                 200                 205

Thr Ser Ile Gln Glu Pro Thr Glu Ile Ser Leu Ser Ser Lys Pro Glu
    210                 215                 220

Pro Arg Gly Pro Thr Ile Lys Pro Cys Pro Pro Cys Lys Cys Pro Ala
225                 230                 235                 240

Pro Asn Leu Leu Gly Gly Pro Ser Val Phe Ile Phe Pro Pro Lys Ile
                245                 250                 255

Lys Asp Val Leu Met Ile Ser Leu Ser Pro Ile Val Thr Cys Val Val
            260                 265                 270

Val Asp Val Ser Glu Asp Asp Pro Asp Val Gln Ile Ser Trp Phe Val
        275                 280                 285

Asn Asn Val Glu Val His Thr Ala Gln Thr Gln Thr His Arg Glu Asp
    290                 295                 300

Tyr Asn Ser Thr Leu Arg Val Val Ser Ala Leu Pro Ile Gln His Gln
305                 310                 315                 320

Asp Trp Met Ser Gly Lys Glu Phe Lys Cys Lys Val Asn Asn Lys Asp
                325                 330                 335

Leu Pro Ala Pro Ile Glu Arg Thr Ile Ser Lys Pro Lys Gly Ser Val
            340                 345                 350

Arg Ala Pro Gln Val Tyr Val Leu Pro Pro Pro Glu Glu Glu Met Thr
        355                 360                 365

Lys Lys Gln Val Thr Leu Thr Cys Met Val Thr Asp Phe Met Pro Glu
    370                 375                 380

Asp Ile Tyr Val Glu Trp Thr Asn Asn Gly Lys Thr Glu Leu Asn Tyr
385                 390                 395                 400

Lys Asn Thr Glu Pro Val Leu Asp Ser Asp Gly Ser Tyr Phe Met Tyr
                405                 410                 415

Ser Lys Leu Arg Val Glu Lys Lys Asn Trp Val Glu Arg Asn Ser Tyr
            420                 425                 430

Ser Cys Ser Val Val His Glu Gly Leu His Asn His His Thr Thr Lys
        435                 440                 445

Ser Phe Ser Arg Thr Pro Gly Lys
```

450 455

<210> SEQ ID NO 5
<211> LENGTH: 468
<212> TYPE: PRT
<213> ORGANISM: Artificial Sequence
<220> FEATURE:
<223> OTHER INFORMATION: Synthetic Sequence_Mouse ANGPTL3(17-455)-His sequence

<400> SEQUENCE: 5

Met Glu Phe Gly Leu Ser Trp Leu Phe Leu Val Ala Ile Leu Lys Gly
1 5 10 15

Val Gln Cys Ser Arg Val Asp Pro Asp Leu Ser Ser Phe Asp Ser Ala
20 25 30

Pro Ser Glu Pro Lys Ser Arg Phe Ala Met Leu Asp Asp Val Lys Ile
35 40 45

Leu Ala Asn Gly Leu Leu Gln Leu Gly His Gly Leu Lys Asp Phe Val
50 55 60

His Lys Thr Lys Gly Gln Ile Asn Asp Ile Phe Gln Lys Leu Asn Ile
65 70 75 80

Phe Asp Gln Ser Phe Tyr Asp Leu Ser Leu Arg Thr Asn Glu Ile Lys
85 90 95

Glu Glu Glu Lys Glu Leu Arg Arg Thr Thr Ser Thr Leu Gln Val Lys
100 105 110

Asn Glu Glu Val Lys Asn Met Ser Val Glu Leu Asn Ser Lys Leu Glu
115 120 125

Ser Leu Leu Glu Glu Lys Thr Ala Leu Gln His Lys Val Arg Ala Leu
130 135 140

Glu Glu Gln Leu Thr Asn Leu Ile Leu Ser Pro Ala Gly Ala Gln Glu
145 150 155 160

His Pro Glu Val Thr Ser Leu Lys Ser Phe Val Glu Gln Gln Asp Asn
165 170 175

Ser Ile Arg Glu Leu Leu Gln Ser Val Glu Glu Gln Tyr Lys Gln Leu
180 185 190

Ser Gln Gln His Met Gln Ile Lys Glu Ile Glu Lys Gln Leu Arg Lys
195 200 205

Thr Gly Ile Gln Glu Pro Ser Glu Asn Ser Leu Ser Ser Lys Ser Arg
210 215 220

Ala Pro Arg Thr Thr Pro Pro Leu Gln Leu Asn Glu Thr Glu Asn Thr
225 230 235 240

Glu Gln Asp Asp Leu Pro Ala Asp Cys Ser Ala Val Tyr Asn Arg Gly
245 250 255

Glu His Thr Ser Gly Val Tyr Thr Ile Lys Pro Arg Asn Ser Gln Gly
260 265 270

Phe Asn Val Tyr Cys Asp Thr Gln Ser Gly Ser Pro Trp Thr Leu Ile
275 280 285

Gln His Arg Lys Asp Gly Ser Gln Asp Phe Asn Glu Thr Trp Glu Asn
290 295 300

Tyr Glu Lys Gly Phe Gly Arg Leu Asp Gly Glu Phe Trp Leu Gly Leu
305 310 315 320

Glu Lys Ile Tyr Ala Ile Val Gln Gln Ser Asn Tyr Ile Leu Arg Leu
325 330 335

Glu Leu Gln Asp Trp Lys Asp Ser Lys His Tyr Val Glu Tyr Ser Phe
340 345 350

```
His Leu Gly Ser His Glu Thr Asn Tyr Thr Leu His Val Ala Glu Ile
        355                 360                 365

Ala Gly Asn Ile Pro Gly Ala Leu Pro Glu His Thr Asp Leu Met Phe
    370                 375                 380

Ser Thr Trp Asn His Arg Ala Lys Gly Gln Leu Tyr Cys Pro Glu Ser
385                 390                 395                 400

Tyr Ser Gly Gly Trp Trp Trp Asn Asp Ile Cys Gly Glu Asn Asn Leu
                405                 410                 415

Asn Gly Lys Tyr Asn Lys Pro Arg Thr Lys Ser Arg Pro Glu Arg Arg
            420                 425                 430

Arg Gly Ile Tyr Trp Arg Pro Gln Ser Arg Lys Leu Tyr Ala Ile Lys
        435                 440                 445

Ser Ser Lys Met Met Leu Gln Pro Thr Thr His His His His His His
    450                 455                 460

His His His His
465


<210> SEQ ID NO 6
<211> LENGTH: 456
<212> TYPE: PRT
<213> ORGANISM: Artificial Sequence
<220> FEATURE:
<223> OTHER INFORMATION: Synthetic Sequence_Mouse ANGPTL3(17-220)-mFc
      sequence

<400> SEQUENCE: 6

Met Glu Phe Gly Leu Ser Trp Leu Phe Leu Val Ala Ile Leu Lys Gly
1               5                   10                  15

Val Gln Cys Ser Arg Val Asp Pro Asp Leu Ser Ser Phe Asp Ser Ala
            20                  25                  30

Pro Ser Glu Pro Lys Ser Arg Phe Ala Met Leu Asp Asp Val Lys Ile
        35                  40                  45

Leu Ala Asn Gly Leu Leu Gln Leu Gly His Gly Leu Lys Asp Phe Val
    50                  55                  60

His Lys Thr Lys Gly Gln Ile Asn Asp Ile Phe Gln Lys Leu Asn Ile
65                  70                  75                  80

Phe Asp Gln Ser Phe Tyr Asp Leu Ser Leu Arg Thr Asn Glu Ile Lys
                85                  90                  95

Glu Glu Glu Lys Glu Leu Arg Arg Thr Thr Ser Thr Leu Gln Val Lys
            100                 105                 110

Asn Glu Glu Val Lys Asn Met Ser Val Glu Leu Asn Ser Lys Leu Glu
        115                 120                 125

Ser Leu Leu Glu Glu Lys Thr Ala Leu Gln His Lys Val Arg Ala Leu
    130                 135                 140

Glu Glu Gln Leu Thr Asn Leu Ile Leu Ser Pro Ala Gly Ala Gln Glu
145                 150                 155                 160

His Pro Glu Val Thr Ser Leu Lys Ser Phe Val Glu Gln Gln Asp Asn
                165                 170                 175

Ser Ile Arg Glu Leu Leu Gln Ser Val Glu Glu Gln Tyr Lys Gln Leu
            180                 185                 190

Ser Gln Gln His Met Gln Ile Lys Glu Ile Glu Lys Gln Leu Arg Lys
        195                 200                 205

Thr Gly Ile Gln Glu Pro Ser Glu Asn Ser Leu Ser Ser Lys Ser Glu
    210                 215                 220

Pro Arg Gly Pro Thr Ile Lys Pro Cys Pro Pro Cys Lys Cys Pro Ala
225                 230                 235                 240
```

Pro Asn Leu Leu Gly Gly Pro Ser Val Phe Ile Phe Pro Pro Lys Ile
245 250 255

Lys Asp Val Leu Met Ile Ser Leu Ser Pro Ile Val Thr Cys Val Val
260 265 270

Val Asp Val Ser Glu Asp Asp Pro Asp Val Gln Ile Ser Trp Phe Val
275 280 285

Asn Asn Val Glu Val His Thr Ala Gln Thr Gln Thr His Arg Glu Asp
290 295 300

Tyr Asn Ser Thr Leu Arg Val Val Ser Ala Leu Pro Ile Gln His Gln
305 310 315 320

Asp Trp Met Ser Gly Lys Glu Phe Lys Cys Lys Val Asn Asn Lys Asp
325 330 335

Leu Pro Ala Pro Ile Glu Arg Thr Ile Ser Lys Pro Lys Gly Ser Val
340 345 350

Arg Ala Pro Gln Val Tyr Val Leu Pro Pro Pro Glu Glu Glu Met Thr
355 360 365

Lys Lys Gln Val Thr Leu Thr Cys Met Val Thr Asp Phe Met Pro Glu
370 375 380

Asp Ile Tyr Val Glu Trp Thr Asn Asn Gly Lys Thr Glu Leu Asn Tyr
385 390 395 400

Lys Asn Thr Glu Pro Val Leu Asp Ser Asp Gly Ser Tyr Phe Met Tyr
405 410 415

Ser Lys Leu Arg Val Glu Lys Lys Asn Trp Val Glu Arg Asn Ser Tyr
420 425 430

Ser Cys Ser Val Val His Glu Gly Leu His Asn His His Thr Thr Lys
435 440 445

Ser Phe Ser Arg Thr Pro Gly Lys
450 455

<210> SEQ ID NO 7
<211> LENGTH: 473
<212> TYPE: PRT
<213> ORGANISM: Artificial Sequence
<220> FEATURE:
<223> OTHER INFORMATION: Synthetic Sequence_Cynomolgus monkey
ANGPTL3(17-460)-His sequence

<400> SEQUENCE: 7

Met Glu Phe Gly Leu Ser Trp Leu Phe Leu Val Ala Ile Leu Lys Gly
1 5 10 15

Val Gln Cys Ser Arg Ile Asp Gln Asp Asn Ser Ser Phe Asp Ser Val
20 25 30

Ser Pro Glu Pro Lys Ser Arg Phe Ala Met Leu Asp Asp Val Lys Ile
35 40 45

Leu Ala Asn Gly Leu Leu Gln Leu Gly His Gly Leu Lys Asp Phe Val
50 55 60

His Lys Thr Lys Gly Gln Ile Asn Asp Ile Phe Gln Lys Leu Asn Ile
65 70 75 80

Phe Asp Gln Ser Phe Tyr Asp Leu Ser Leu Gln Thr Ser Glu Ile Lys
85 90 95

Glu Glu Glu Lys Glu Leu Arg Arg Thr Thr Tyr Lys Leu Gln Val Lys
100 105 110

Asn Glu Glu Val Lys Asn Met Ser Leu Glu Leu Asn Ser Lys Leu Glu
115 120 125

Ser Leu Leu Glu Glu Lys Ile Leu Leu Gln Gln Lys Val Lys Tyr Leu

```
    130                 135                 140

Glu Glu Gln Leu Thr Asn Leu Ile Gln Asn Gln Pro Ala Thr Pro Glu
145                 150                 155                 160

His Pro Glu Val Thr Ser Leu Lys Ser Phe Val Glu Lys Gln Asp Asn
                165                 170                 175

Ser Ile Lys Asp Leu Leu Gln Thr Val Glu Glu Gln Tyr Lys Gln Leu
            180                 185                 190

Asn Gln Gln His Ser Gln Ile Lys Glu Ile Glu Asn Gln Leu Arg Met
        195                 200                 205

Thr Asn Ile Gln Glu Pro Thr Glu Ile Ser Leu Ser Ser Lys Pro Arg
    210                 215                 220

Ala Pro Arg Thr Thr Pro Phe Leu Gln Leu Asn Glu Ile Arg Asn Val
225                 230                 235                 240

Lys His Asp Gly Ile Pro Ala Asp Cys Thr Thr Ile Tyr Asn Arg Gly
                245                 250                 255

Glu His Ile Ser Gly Thr Tyr Ala Ile Arg Pro Ser Asn Ser Gln Val
            260                 265                 270

Phe His Val Tyr Cys Asp Val Val Ser Gly Ser Pro Trp Thr Leu Ile
        275                 280                 285

Gln His Arg Ile Asp Gly Ser Gln Asn Phe Asn Glu Thr Trp Glu Asn
    290                 295                 300

Tyr Lys Tyr Gly Phe Gly Arg Leu Asp Gly Glu Phe Trp Leu Gly Leu
305                 310                 315                 320

Glu Lys Ile Tyr Ser Ile Val Lys Gln Ser Asn Tyr Val Leu Arg Ile
                325                 330                 335

Glu Leu Glu Asp Trp Lys Asp Asn Lys His Tyr Ile Glu Tyr Ser Phe
            340                 345                 350

Tyr Leu Gly Asn His Glu Thr Asn Tyr Thr Leu His Val Val Lys Ile
        355                 360                 365

Thr Gly Asn Val Pro Asn Ala Ile Pro Glu Asn Lys Asp Leu Val Phe
    370                 375                 380

Ser Thr Trp Asp His Lys Ala Lys Gly His Phe Ser Cys Pro Glu Ser
385                 390                 395                 400

Tyr Ser Gly Gly Trp Trp Trp His Asp Glu Cys Gly Glu Asn Asn Leu
                405                 410                 415

Asn Gly Lys Tyr Asn Lys Pro Arg Thr Lys Ser Lys Pro Glu Arg Arg
            420                 425                 430

Arg Gly Leu Ser Trp Lys Ser Gln Asn Gly Arg Leu Tyr Ser Ile Lys
        435                 440                 445

Ser Thr Lys Met Leu Ile His Pro Thr Asp Ser Glu Ser Phe Glu His
    450                 455                 460

His His His His His His His His His
465                 470
```

<210> SEQ ID NO 8
<211> LENGTH: 468
<212> TYPE: PRT
<213> ORGANISM: Artificial Sequence
<220> FEATURE:
<223> OTHER INFORMATION: Synthetic Sequence_Rat ANGPTL3(17-455)-His sequence

<400> SEQUENCE: 8

```
Met Glu Phe Gly Leu Ser Trp Leu Phe Leu Val Ala Ile Leu Lys Gly
1               5                   10                  15
```

-continued

```
Val Gln Cys Ser Arg Val Asp Pro Asp Leu Ser Pro Phe Asp Ser Val
            20                  25                  30

Pro Ser Glu Pro Lys Ser Arg Phe Ala Met Leu Asp Asp Val Lys Ile
        35                  40                  45

Leu Ala Asn Gly Leu Leu Gln Leu Gly His Gly Leu Lys Asp Phe Val
    50                  55                  60

His Lys Thr Lys Gly Gln Ile Asn Asp Ile Phe Gln Lys Leu Asn Ile
65                  70                  75                  80

Phe Asp Gln Cys Phe Tyr Asp Leu Ser Leu Gln Thr Asn Glu Ile Lys
                85                  90                  95

Glu Glu Glu Lys Glu Leu Arg Arg Thr Thr Ser Lys Leu Gln Val Lys
            100                 105                 110

Asn Glu Glu Val Lys Asn Met Ser Leu Glu Leu Asn Ser Lys Leu Glu
        115                 120                 125

Ser Leu Leu Glu Glu Lys Met Ala Leu Gln His Arg Val Arg Ala Leu
    130                 135                 140

Glu Glu Gln Leu Thr Ser Leu Val Gln Asn Pro Pro Gly Ala Arg Glu
145                 150                 155                 160

His Pro Glu Val Thr Ser Leu Lys Ser Phe Val Glu Gln Gln Asp Asn
                165                 170                 175

Ser Ile Arg Glu Leu Leu Gln Ser Val Glu Glu Gln Tyr Lys Gln Leu
            180                 185                 190

Ser Gln Gln His Ile Gln Ile Lys Glu Ile Glu Asn Gln Leu Arg Lys
        195                 200                 205

Thr Gly Ile Gln Glu Pro Thr Glu Asn Ser Leu Tyr Ser Lys Pro Arg
    210                 215                 220

Ala Pro Arg Thr Thr Pro Pro Leu His Leu Lys Glu Ala Lys Asn Ile
225                 230                 235                 240

Glu Gln Asp Asp Leu Pro Ala Asp Cys Ser Ala Ile Tyr Asn Arg Gly
                245                 250                 255

Glu His Thr Ser Gly Val Tyr Thr Ile Arg Pro Ser Ser Ser Gln Val
            260                 265                 270

Phe Asn Val Tyr Cys Asp Thr Gln Ser Gly Thr Pro Arg Thr Leu Ile
        275                 280                 285

Gln His Arg Lys Asp Gly Ser Gln Asn Phe Asn Gln Thr Trp Glu Asn
    290                 295                 300

Tyr Glu Lys Gly Phe Gly Arg Leu Asp Gly Glu Phe Trp Leu Gly Leu
305                 310                 315                 320

Glu Lys Ile Tyr Ala Ile Val Lys Gln Ser Asn Tyr Ile Leu Arg Leu
                325                 330                 335

Glu Leu Gln Asp Trp Lys Asp Ser Lys His Tyr Ala Glu Tyr Ser Phe
            340                 345                 350

His Leu Gly Asn His Glu Thr Asn Tyr Thr Leu His Val Ala Glu Ile
        355                 360                 365

Ala Ala Asn Ile Pro Glu Ala Leu Pro Glu His Arg Asp Leu Met Phe
    370                 375                 380

Ser Thr Trp Asp His Arg Ala Lys Gly Gln Leu Tyr Cys Pro Glu Ser
385                 390                 395                 400

Tyr Ser Gly Gly Trp Trp Phe Ser Asp Met Cys Gly Glu Asn Asn Leu
                405                 410                 415

Asn Gly Lys Tyr Asn Lys Pro Arg Ala Lys Ser Lys Pro Glu Arg Arg
            420                 425                 430

Arg Gly Ile Ser Trp Arg Pro Arg Gly Gly Lys Leu Tyr Ser Ile Lys
```

```
        435                 440                 445

Ser Ser Lys Met Met Leu Gln Pro Thr Thr His His His His His His
    450                 455                 460

His His His His
465


<210> SEQ ID NO 9
<211> LENGTH: 124
<212> TYPE: PRT
<213> ORGANISM: Artificial Sequence
<220> FEATURE:
<223> OTHER INFORMATION: Synthetic Sequence_Heavy chain variable region
      sequence of P3

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ser Ser Gly Tyr Thr Phe Thr Asp Tyr
            20                  25                  30

Tyr Leu His Trp Leu Arg Gln Ala Pro Gly Gln Gly Pro Glu Trp Met
        35                  40                  45

Gly Trp Ile Ser Pro Asn Ser Gly Gly Thr Ser Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Asp Ile Ala Thr Leu Gly Asn Phe Phe Thr Tyr Gly Met Asp
            100                 105                 110

Val Trp Gly Gln Gly Thr Thr Val Thr Val Ser Ser
        115                 120


<210> SEQ ID NO 10
<211> LENGTH: 106
<212> TYPE: PRT
<213> ORGANISM: Artificial Sequence
<220> FEATURE:
<223> OTHER INFORMATION: Synthetic Sequence_Light chain variable region
      sequence of P3

<400> SEQUENCE: 10

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Trp Thr
                85                  90                  95

Phe Gly Gln Gly Thr Lys Val Glu Ile Lys
            100                 105


<210> SEQ ID NO 11
<211> LENGTH: 124
<212> TYPE: PRT
```

```
<213> ORGANISM: Artificial Sequence
<220> FEATURE:
<223> OTHER INFORMATION: Synthetic Sequence_Heavy chain variable region
      sequence of P8

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Val
        35                  40                  45

Gly Leu Ile Asn Pro Arg Asp Asp Ser Thr Ser Tyr Ala Gln Lys Phe
    50                  55                  60

Gln Gly Arg Val Thr Met Thr Arg Asp Thr Ser Thr Ser Thr Met Tyr
65                  70                  75                  80

Met Glu Leu Ser Ser Leu Arg Ser Glu Asp Thr Ala Val Tyr Phe Cys
                85                  90                  95

Ala Arg Asp Leu Gly Ser Ile Arg Glu Val Leu Tyr Tyr Gly Met Asp
            100                 105                 110

Val Trp Gly Gln Gly Thr Thr Val Thr Val Ser Ser
        115                 120


<210> SEQ ID NO 12
<211> LENGTH: 112
<212> TYPE: PRT
<213> ORGANISM: Artificial Sequence
<220> FEATURE:
<223> OTHER INFORMATION: Synthetic Sequence_Light chain variable region
      sequence of P8

<400> SEQUENCE: 12

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Thr Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gln Gly Thr Arg Leu Glu Ile Lys
            100                 105                 110


<210> SEQ ID NO 13
<211> LENGTH: 124
<212> TYPE: PRT
<213> ORGANISM: Artificial Sequence
<220> FEATURE:
<223> OTHER INFORMATION: Synthetic Sequence_Heavy chain variable region
      sequence of P8B

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

```
Asp Ile Asn Trp Val Arg Gln Ala Pro Gly Gln Gly Leu Glu Trp Val
        35                  40                  45

Gly Leu Ile Asn Pro Arg Glu Asp Ser Thr Ser Tyr Ala Gln Lys Phe
    50                  55                  60

Gln Gly Arg Val Thr Met Thr Arg Asp Thr Ser Thr Ser Thr Met Tyr
65                  70                  75                  80

Met Glu Leu Ser Ser Leu Arg Ser Glu Asp Thr Ala Val Tyr Phe Cys
                85                  90                  95

Ala Arg Asp Leu Gly Ser Ile Arg Glu Val Leu Tyr Tyr Gly Met Asp
            100                 105                 110

Val Trp Gly Gln Gly Thr Thr Val Thr Val Ser Ser
        115                 120


<210> SEQ ID NO 14
<211> LENGTH: 112
<212> TYPE: PRT
<213> ORGANISM: Artificial Sequence
<220> FEATURE:
<223> OTHER INFORMATION: Synthetic Sequence_Light chain variable region
      sequence of P8B

<400> SEQUENCE: 14

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Val Tyr Thr Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gln Gly Thr Arg Leu Glu Ile Lys
            100                 105                 110


<210> SEQ ID NO 15
<211> LENGTH: 11
<212> TYPE: PRT
<213> ORGANISM: Artificial Sequence
<220> FEATURE:
<223> OTHER INFORMATION: Synthetic Sequence_LCDR1 sequence of P3

<400> SEQUENCE: 15

Arg Ala Ser Gln Gly Ile Arg Asn Asp Leu Gly
1               5                   10


<210> SEQ ID NO 16
<211> LENGTH: 7
<212> TYPE: PRT
<213> ORGANISM: Artificial Sequence
<220> FEATURE:
<223> OTHER INFORMATION: Synthetic Sequence_LCDR2 sequence of P3

<400> SEQUENCE: 16

Ala Ala Ser Ser Leu Gln Ser
1               5


<210> SEQ ID NO 17
```

<211> LENGTH: 8
<212> TYPE: PRT
<213> ORGANISM: Artificial Sequence
<220> FEATURE:
<223> OTHER INFORMATION: Synthetic Sequence_LCDR3 sequence of P3

<400> SEQUENCE: 17

Gln Gln Ser Tyr Ser Ser Trp Thr
1 5

<210> SEQ ID NO 18
<211> LENGTH: 5
<212> TYPE: PRT
<213> ORGANISM: Artificial Sequence
<220> FEATURE:
<223> OTHER INFORMATION: Synthetic Sequence_HCDR1 sequence of P3

<400> SEQUENCE: 18

Asp Tyr Tyr Leu His
1 5

<210> SEQ ID NO 19
<211> LENGTH: 17
<212> TYPE: PRT
<213> ORGANISM: Artificial Sequence
<220> FEATURE:
<223> OTHER INFORMATION: Synthetic Sequence_HCDR2 sequence of P3

<400> SEQUENCE: 19

Trp Ile Ser Pro Asn Ser Gly Gly Thr Ser Tyr Ala Gln Lys Phe Gln
1 5 10 15

Gly

<210> SEQ ID NO 20
<211> LENGTH: 15
<212> TYPE: PRT
<213> ORGANISM: Artificial Sequence
<220> FEATURE:
<223> OTHER INFORMATION: Synthetic Sequence_HCDR3 sequence of P3

<400> SEQUENCE: 20

Asp Ile Ala Thr Leu Gly Asn Phe Phe Thr Tyr Gly Met Asp Val
1 5 10 15

<210> SEQ ID NO 21
<211> LENGTH: 16
<212> TYPE: PRT
<213> ORGANISM: Artificial Sequence
<220> FEATURE:
<223> OTHER INFORMATION: Synthetic Sequence_LCDR1 sequence of P8

<400> SEQUENCE: 21

Arg Ser Ser Gln Ser Leu Leu His Ser Asn Gly Tyr Thr Tyr Leu Asp
1 5 10 15

<210> SEQ ID NO 22
<211> LENGTH: 7
<212> TYPE: PRT
<213> ORGANISM: Artificial Sequence
<220> FEATURE:
<223> OTHER INFORMATION: Synthetic Sequence_LCDR2 sequence of P8/P8B

<400> SEQUENCE: 22

Leu Gly Ser Asn Arg Ala Ser
1 5

<210> SEQ ID NO 23
<211> LENGTH: 9
<212> TYPE: PRT
<213> ORGANISM: Artificial Sequence
<220> FEATURE:
<223> OTHER INFORMATION: Synthetic Sequence_LCDR3 sequence of P8/P8B

<400> SEQUENCE: 23

Met Gln Ala Leu Gln Thr Pro Leu Thr
1 5

<210> SEQ ID NO 24
<211> LENGTH: 5
<212> TYPE: PRT
<213> ORGANISM: Artificial Sequence
<220> FEATURE:
<223> OTHER INFORMATION: Synthetic Sequence_HCDR1 sequence of P8/P8B

<400> SEQUENCE: 24

Ser Tyr Asp Ile Asn
1 5

<210> SEQ ID NO 25
<211> LENGTH: 17
<212> TYPE: PRT
<213> ORGANISM: Artificial Sequence
<220> FEATURE:
<223> OTHER INFORMATION: Synthetic Sequence_HCDR2 sequence of P8

<400> SEQUENCE: 25

Leu Ile Asn Pro Arg Asp Asp Ser Thr Ser Tyr Ala Gln Lys Phe Gln
1 5 10 15

Gly

<210> SEQ ID NO 26
<211> LENGTH: 15
<212> TYPE: PRT
<213> ORGANISM: Artificial Sequence
<220> FEATURE:
<223> OTHER INFORMATION: Synthetic Sequence_HCDR3 sequence of P8/P8B

<400> SEQUENCE: 26

Asp Leu Gly Ser Ile Arg Glu Val Leu Tyr Tyr Gly Met Asp Val
1 5 10 15

<210> SEQ ID NO 27
<211> LENGTH: 16
<212> TYPE: PRT
<213> ORGANISM: Artificial Sequence
<220> FEATURE:
<223> OTHER INFORMATION: Synthetic Sequence_LCDR1 sequence of P8B

<400> SEQUENCE: 27

Arg Ser Ser Gln Ser Leu Leu His Ser Asn Val Tyr Thr Tyr Leu Asp
1 5 10 15

<210> SEQ ID NO 28
<211> LENGTH: 17
<212> TYPE: PRT
<213> ORGANISM: Artificial Sequence
<220> FEATURE:
<223> OTHER INFORMATION: Synthetic Sequence_HCDR2 sequence of P8B

<400> SEQUENCE: 28

Leu Ile Asn Pro Arg Glu Asp Ser Thr Ser Tyr Ala Gln Lys Phe Gln
1 5 10 15

Gly

<210> SEQ ID NO 29
<211> LENGTH: 327
<212> TYPE: PRT
<213> ORGANISM: Artificial Sequence
<220> FEATURE:
<223> OTHER INFORMATION: Synthetic Sequence_Heavy chain constant region sequence of human IgG4-YTE variant

<400> SEQUENCE: 29

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Lys Thr
65 70 75 80

Tyr Thr Cys Asn Val Asp His Lys Pro Ser Asn Thr Lys Val Asp Lys
85 90 95

Arg Val Glu Ser Lys Tyr Gly Pro Pro Cys Pro Pro Cys Pro Ala Pro
100 105 110

Glu Phe Leu Gly Gly Pro Ser Val Phe Leu Phe Pro Pro Lys Pro Lys
115 120 125

Asp Thr Leu Tyr Ile Thr Arg Glu Pro Glu Val Thr Cys Val Val Val
130 135 140

Asp Val Ser Gln Glu Asp Pro Glu Val Gln Phe Asn Trp Tyr Val Asp
145 150 155 160

Gly Val Glu Val His Asn Ala Lys Thr Lys Pro Arg Glu Glu Gln Phe
165 170 175

Asn Ser Thr Tyr Arg Val Val Ser Val Leu Thr Val Leu His Gln Asp
180 185 190

Trp Leu Asn Gly Lys Glu Tyr Lys Cys Lys Val Ser Asn Lys Gly Leu
195 200 205

Pro Ser Ser Ile Glu Lys Thr Ile Ser Lys Ala Lys Gly Gln Pro Arg
210 215 220

Glu Pro Gln Val Tyr Thr Leu Pro Pro Ser Gln Glu Glu Met Thr Lys
225 230 235 240

Asn Gln Val Ser Leu Thr Cys Leu Val Lys Gly Phe Tyr Pro Ser Asp
245 250 255

Ile Ala Val Glu Trp Glu Ser Asn Gly Gln Pro Glu Asn Asn Tyr Lys
260 265 270

Thr Thr Pro Pro Val Leu Asp Ser Asp Gly Ser Phe Phe Leu Tyr Ser
275 280 285

Arg Leu Thr Val Asp Lys Ser Arg Trp Gln Glu Gly Asn Val Phe Ser
290 295 300

Cys Ser Val Met His Glu Ala Leu His Asn His Tyr Thr Gln Lys Ser
305 310 315 320

Leu Ser Leu Ser Leu Gly Lys
325

<210> SEQ ID NO 30
<211> LENGTH: 107

<212> TYPE: PRT
<213> ORGANISM: Artificial Sequence
<220> FEATURE:
<223> OTHER INFORMATION: Synthetic Sequence_Light chain constant region sequence of human kappa chain

<400> SEQUENCE: 30

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 31
<211> LENGTH: 451
<212> TYPE: PRT
<213> ORGANISM: Artificial Sequence
<220> FEATURE:
<223> OTHER INFORMATION: Synthetic Sequence_Heavy chain sequence of P3G

<400> SEQUENCE: 31

```
Gln Val Gln Leu Val Gln Ser Gly Ala Glu Val Lys Lys Pro Gly Ala
1               5                   10                  15

Ser Val Lys Val Ser Cys Lys Ser Ser Gly Tyr Thr Phe Thr Asp Tyr
            20                  25                  30

Tyr Leu His Trp Leu Arg Gln Ala Pro Gly Gln Gly Pro Glu Trp Met
        35                  40                  45

Gly Trp Ile Ser Pro Asn Ser Gly Gly Thr Ser Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Asp Ile Ala Thr Leu Gly Asn Phe Phe Thr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
```

```
    210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Tyr
                245                 250                 255

Ile Thr Arg Glu Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450


<210> SEQ ID NO 32
<211> LENGTH: 213
<212> TYPE: PRT
<213> ORGANISM: Artificial Sequence
<220> FEATURE:
<223> OTHER INFORMATION: Synthetic Sequence_Light chain sequence of P3G

<400> SEQUENCE: 32

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
```

```
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 33
<211> LENGTH: 451
<212> TYPE: PRT
<213> ORGANISM: Artificial Sequence
<220> FEATURE:
<223> OTHER INFORMATION: Synthetic Sequence_Heavy chain sequence of P8G

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Val
        35                  40                  45

Gly Leu Ile Asn Pro Arg Asp Asp Ser Thr Ser Tyr Ala Gln Lys Phe
    50                  55                  60

Gln Gly Arg Val Thr Met Thr Arg Asp Thr Ser Thr Ser Thr Met Tyr
65                  70                  75                  80

Met Glu Leu Ser Ser Leu Arg Ser Glu Asp Thr Ala Val Tyr Phe Cys
                85                  90                  95

Ala Arg Asp Leu Gly Ser Ile Arg Glu Val Leu Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Tyr
                245                 250                 255

Ile Thr Arg Glu Pro Glu Val Thr Cys Val Val Val Asp Val Ser Gln
```

```
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450


<210> SEQ ID NO 34
<211> LENGTH: 219
<212> TYPE: PRT
<213> ORGANISM: Artificial Sequence
<220> FEATURE:
<223> OTHER INFORMATION: Synthetic Sequence_Light chain sequence of P8G

<400> SEQUENCE: 34

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Thr Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gln Gly Thr Arg Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
```

```
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 35
<211> LENGTH: 451
<212> TYPE: PRT
<213> ORGANISM: Artificial Sequence
<220> FEATURE:
<223> OTHER INFORMATION: Synthetic Sequence_Heavy chain sequence of P8BG

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Val
        35                  40                  45

Gly Leu Ile Asn Pro Arg Glu Asp Ser Thr Ser Tyr Ala Gln Lys Phe
    50                  55                  60

Gln Gly Arg Val Thr Met Thr Arg Asp Thr Ser Thr Ser Thr Met Tyr
65                  70                  75                  80

Met Glu Leu Ser Ser Leu Arg Ser Glu Asp Thr Ala Val Tyr Phe Cys
                85                  90                  95

Ala Arg Asp Leu Gly Ser Ile Arg Glu Val Leu Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Tyr
                245                 250                 255

Ile Thr Arg Glu Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
```

305 310 315 320

Lys Glu Tyr Lys Cys Lys Val Ser Asn Lys Gly Leu Pro Ser Ser Ile
325 330 335

Glu Lys Thr Ile Ser Lys Ala Lys Gly Gln Pro Arg Glu Pro Gln Val
340 345 350

Tyr Thr Leu Pro Pro Ser Gln Glu Glu Met Thr Lys Asn Gln Val Ser
355 360 365

Leu Thr Cys Leu Val Lys Gly Phe Tyr Pro Ser Asp Ile Ala Val Glu
370 375 380

Trp Glu Ser Asn Gly Gln Pro Glu Asn Asn Tyr Lys Thr Thr Pro Pro
385 390 395 400

Val Leu Asp Ser Asp Gly Ser Phe Phe Leu Tyr Ser Arg Leu Thr Val
405 410 415

Asp Lys Ser Arg Trp Gln Glu Gly Asn Val Phe Ser Cys Ser Val Met
420 425 430

His Glu Ala Leu His Asn His Tyr Thr Gln Lys Ser Leu Ser Leu Ser
435 440 445

Leu Gly Lys
450

<210> SEQ ID NO 36
<211> LENGTH: 219
<212> TYPE: PRT
<213> ORGANISM: Artificial Sequence
<220> FEATURE:
<223> OTHER INFORMATION: Synthetic Sequence_Light chain sequence of P8BG

<400> SEQUENCE: 36

Asp Val Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Val Tyr Thr Tyr Leu Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Thr Pro Leu Thr Phe Gly Gln Gly Thr Arg Leu Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

-continued

```
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

ANTI-ANGIOPOIETIN-LIKE PROTEIN 3 (ANGPTL3) ANTIBODY AND PHARMACEUTICAL COMPOSITION THEREOF

CROSS-REFERENCE TO RELATED APPLICATIONS

The present application is a national stage application of International Patent Application No. PCT/CN2021/073239, filed Jan. 22, 2021, which claims the benefit of and priority to the Chinese Patent Application No. 202010073192.4 filed Jan. 22, 2020, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jun. 24, 2022 is named "721011CPUS_126268-5037-US_ST25_Sequence_Listing.txt" and is 62,633 bytes in size.

TECHNICAL FIELD

The present disclosure relates to the field of antibody drugs. Specifically, an anti-angiopoietin-like protein 3(ANGPTL3) antibody drug and use thereof are included.

BACKGROUND

The statement herein merely provide background information related to the present invention and may not necessarily constitute the prior art.

The angiopoietin-like protein 3 (ANGPTL3, ANGPTL-3) gene is a novel gene identified by Conklin et al. from EST databases based on signal sequences and amphipathic helices, and they isolated the full-length cDNA of human ANGPTL3 from a human fetal liver/spleen cDNA library (Conklin et al., 1999*, Genomics* 62: 477-482). The 460-amino acid human ANGPTL3 protein (hANGPTL3) shares 76% amino acid sequence identity with mouse ANGPTL3 protein and has the characteristic structure of angiopoietins: a signal peptide, an extended helical domain predicted to form dimeric or trimeric coiled-coils, a short linker peptide, and a globular fibrinogen homology domain (FD) (Conklin et al., 1999*, Genomics* 62: 477-482). ANGPTL3 is different from angiopoietins (ANGs), and ANGPTL3 does not bind to Tie2. However, it can also induce angiogenesis by binding to integrin αvβ via its C-terminal FD (Camenisch et al., 2002*, J Biol Chem* 277: 17281-17290).

In addition, ANGPTL3 is an important factor affecting fat metabolism. ANGPTL3 can inhibit LPL activity, thereby reducing clearance of triglycerides and low density lipoproteins, while hypertriglyceridemia is involved in the pathogenesis of a range of metabolic diseases. Elevated plasma triglyceride level can be implicated in the pathological process of atherosclerosis by inducing platelet aggregation and the production of plasminogen activator inhibitor-1 (PAI-1), increasing the number of foam cells and promoting the proliferation and migration of vascular smooth muscle cells. The anti-ANGPTL3 antibody can specifically bind to ANGPTL3, so that the ANGPTL3 activity can be inhibited or interfered with, and thus diseases such as atherosclerosis and hyperlipidemia can be treated. At present, various anti-ANGPTL3 antibodies have been disclosed in patent documents such as WO2012174178A1, WO2008073300A2 and CN107085112A.

SUMMARY

The present disclosure provides an anti-angiopoietin-like protein 3(ANGPTL3) antibody or an antigen-binding fragment thereof. In some embodiments, the present disclosure provides an anti-ANGPTL3 antibody or an antigen-binding fragment thereof, which comprises a heavy chain variable region and a light chain variable region of an antibody, wherein:

i) the heavy chain variable region comprises an HCDR1, an HCDR2 and an HCDR3 identical in sequences to those of a heavy chain variable region set forth in SEQ ID NO: 9, and the light chain variable region comprises an LCDR1, an LCDR2 and an LCDR3 identical in sequences to those of a light chain variable region set forth in SEQ ID NO: 10;

ii) the heavy chain variable region comprises an HCDR1, an HCDR2 and an HCDR3 identical in sequences to those of a heavy chain variable region set forth in SEQ ID NO: 11, and the light chain variable region comprises an LCDR1, an LCDR2 and an LCDR3 identical in sequences to those of a light chain variable region set forth in SEQ ID NO: 12; or iii) the heavy chain variable region comprises an HCDR1, an HCDR2 and an HCDR3 identical in sequences to those of a heavy chain variable region set forth in SEQ ID NO: 13, and the light chain variable region comprises an LCDR1, an LCDR2 and an LCDR3 identical in sequences to those of a light chain variable region set forth in SEQ ID NO: 14.

In some embodiments, provided is the anti-ANGPTL3 antibody or the antigen-binding fragment thereof described above, which comprises a heavy chain variable region and a light chain variable region, wherein:

iv) the heavy chain variable region comprises an HCDR1, an HCDR2 and an HCDR3 having sequences set forth in SEQ ID NO: 18, SEQ ID NO: 19 and SEQ ID NO: 20, respectively, and the light chain variable region comprises an LCDR1, an LCDR2 and an LCDR3 having sequences set forth in SEQ ID NO: 15, SEQ ID NO: 16 and SEQ ID NO: 17, respectively;

v) the heavy chain variable region comprises an HCDR1, an HCDR2 and an HCDR3 having sequences set forth in SEQ ID NO: 24, SEQ ID NO: 25 and SEQ ID NO: 26, respectively, and the light chain variable region comprises an LCDR1, an LCDR2 and an LCDR3 having sequences set forth in SEQ ID NO: 21, SEQ ID NO: 22 and SEQ ID NO: 23, respectively; or vi) the heavy chain variable region comprises an HCDR1, an HCDR2 and an HCDR3 having sequences set forth in SEQ ID NO: 24, SEQ ID NO: 28 and SEQ ID NO: 26, respectively, and the light chain variable region comprises an LCDR1, an LCDR2 and an LCDR3 having sequences set forth in SEQ ID NO: 27, SEQ ID NO: 22 and SEQ ID NO: 23, respectively. In some embodiments, provided is the anti-ANGPTL3 antibody or the antigen-binding fragment thereof described above, which comprises a heavy chain variable region and a light chain variable region, wherein:

(A) the heavy chain variable region has at least 90%, 91%, 92%, 93%, 94%, 95%, 96%, 97%, 98% or 99% identity to a sequence set forth in SEQ ID NO: 9, and/or the light chain variable region has at least 90%, 91%, 92%, 93%, 94%, 95%, 96%, 97%, 98% or 99% identity to a sequence set forth in SEQ ID NO: 10;

(B) the heavy chain variable region has at least 90%, 91%, 92%, 93%, 94%, 95%, 96%, 97%, 98% or 99% identity to a sequence set forth in SEQ ID NO: 11, and/or the light chain variable region has at least 90%, 91%, 92%, 93%, 94%, 95%, 96%, 97%, 98% or 99% identity to a sequence set forth in SEQ ID NO: 12; or (C) the heavy chain variable region has at least 90%, 91%, 92%, 93%, 94%, 95%, 96%, 97%, 98% or 99% identity to a sequence set forth in SEQ ID NO: 13, and/or the light chain variable region has at least 90%, 91%, 92%, 93%, 94%, 95%, 96%, 97%, 98% or 99% identity to a sequence set forth in SEQ ID NO: 14.

In some embodiments, provided is the anti-ANGPTL3 antibody or the antigen-binding fragment thereof described above, which comprises a heavy chain variable region and a light chain variable region shown below:

(D) the heavy chain variable region has a sequence set forth in SEQ ID NO: 9, and the light chain variable region has a sequence set forth in SEQ ID NO: 10;

(E) the heavy chain variable region has a sequence set forth in SEQ ID NO: 11, and the light chain variable region has a sequence set forth in SEQ ID NO: 12; or (F) the heavy chain variable region has a sequence set forth in SEQ ID NO: 13, and the light chain variable region has a sequence set forth in SEQ ID NO: 14.

In some embodiments, provided is the anti-ANGPTL3 antibody or the antigen-binding fragment thereof described above, wherein the anti-ANGPTL3 antibody further comprises a heavy chain constant region and a light chain constant region; in some embodiments, the heavy chain constant region is selected from the group consisting of human IgG1, IgG2, IgG3 and IgG4 constant regions, and the light chain constant region is selected from the group consisting of human κ chain and λ chain constant regions; in some embodiments, the heavy chain constant region has a sequence set forth in SEQ ID NO: 29 or a sequence having at least 85%, 86%, 87%, 88%, 89%, 90%, 91%, 92%, 93%, 94%, 95%, 96%, 97%, 98% or 99% sequence identity to the sequence set forth in SEQ ID NO. 29, and/or the light chain constant region has a sequence set forth in SEQ ID NO: 30 or a sequence having at least 85%, 86%, 87%, 88%, 89%, 90%, 91%, 92%, 93%, 94%, 95%, 96%, 97%, 98% or 99% sequence identity to the sequence set forth in SEQ ID NO. 30. In some embodiments, provided is the anti-ANGPTL3 antibody or the antigen-binding fragment thereof described above, wherein the anti-ANGPTL3 antibody comprises a heavy chain and a light chain, wherein, (G) the heavy chain has at least 85%, 86%, 87%, 88%, 89%, 90%, 91%, 92%, 93%, 94%, 95%, 96%, 97%, 98% or 99% identity to a sequence set forth in SEQ ID NO: 31, and/or the light chain has at least 85%, 86%, 87%, 88%, 89%, 90%, 91%, 92%, 93%, 94%, 95%, 96%, 97%, 98% or 99% identity to a sequence set forth in SEQ ID NO: 32;

(H) the heavy chain has at least 85%, 86%, 87%, 88%, 89%, 90%, 91%, 92%, 93%, 94%, 95%, 96%, 97%, 98% or 99% identity to a sequence set forth in SEQ ID NO: 33, and/or the light chain has at least 85%, 86%, 87%, 88%, 89%, 90%, 91%, 92%, 93%, 94%, 95%, 96%, 97%, 98% or 99% identity to a sequence set forth in SEQ ID NO: 34; or (I) the heavy chain has at least 85%, 86%, 87%, 88%, 89%, 90%, 91%, 92%, 93%, 94%, 95%, 96%, 97%, 98% or 99% identity to a sequence set forth in SEQ ID NO: 35, and/or the light chain has at least 85%, 86%, 87%, 88%, 89%, 90%, 91%, 92%, 93%, 94%, 95%, 96%, 97%, 98% or 99% identity to a sequence set forth in SEQ ID NO: 36.

In some embodiments, provided is the anti-ANGPTL3 antibody or the antigen-binding fragment thereof described above, wherein the anti-ANGPTL3 antibody comprises a heavy chain and a light chain, wherein, (J) the heavy chain has a sequence set forth in SEQ ID NO: 31, and the light chain has a sequence set forth in SEQ ID NO: 32;

(K) the heavy chain has a sequence set forth in SEQ ID NO: 33, and the light chain has a sequence set forth in SEQ ID NO: 34; or (L) the heavy chain has a sequence set forth in SEQ ID NO: 35, and the light chain has a sequence set forth in SEQ ID NO: 36.

In some embodiments, the present disclosure provides an isolated anti-ANGPTL3 antibody or an antigen-binding fragment thereof, wherein the anti-ANGPTL3 antibody or the antigen-binding fragment thereof competes with an anti-ANGPTL3 antibody or the antigen-binding fragment thereof described above for binding to an ANGPTL3 antigen. In some embodiments, the ANGPTL3 antigen is human ANGPTL3, mouse ANGPTL3, monkey ANGPTL3 or rat ANGPTL3.

In some embodiments, an antibody described herein is a human antibody or a human-derived antibody. In some embodiments, the antigen-binding fragment described herein is selected from the group consisting of Fab, $F(ab')_2$, Fab', Fd, Fv, dsFv, scFv, Fab and a diabody. In some embodiments, the anti-ANGPTL3 antibody or the antigen-binding fragment thereof of the present disclosure has at least one of the following characteristics a-d:

a. Specifically binding to an ANGPTL3 protein. In some embodiments, the anti-ANGPTL3 antibody or the antigen-binding fragment thereof binds to human ANGPTL3, mouse ANGPTL3, cynomolgus monkey ANGPTL3 and/or rat ANGPT3L with an $EC_{50}$ of less than 10 nM (e.g., less than or equal to 5 nM, less than or equal to 3 nM, less than or equal to 1 nM, less than or equal to 0.8 nM, less than or equal to 0.6 nM, less than or equal to 0.4 nM, less than or equal to 0.3 nM, or less than or equal to 0.2 nM); in some embodiments, the $EC_{50}$ is determined by the ELISA method, e.g., as described in Test Example 1 of the present disclosure; in some embodiments, the $EC_{50}$ is determined by the HTRF method, e.g., as described in Test Example 2 of the present disclosure;

b. Binding to an ANGPTL3 protein with high affinity. In some embodiments, the anti-ANGPTL3 antibody or the antigen-binding fragment thereof binds to human ANGPTL3, mouse ANGPTL3, cynomolgus monkey ANGPTL3 and/or rat ANGPTL3 antigen with a KD value of less than 10E−10 M (e.g., less than or equal to 9E−10 M, less than or equal to 8E−10 M, less than or equal to 7E−10 M, less than or equal to 6E−10 M, less than or equal to 3E−10 M, less than or equal to 2E−10 M, less than or equal to 1E−10 M, less than or equal to 8E−11 M, less than or equal to 6E−11 M, or less than or equal to 5E−11 M); in some embodiments, the KD value is determined by the Biacore method, e.g., as described in Test Example 4 of the present disclosure;

c. Blocking the inhibition of ANGPTL3 against LPL enzyme. In some embodiments, the anti-ANGPTL3 antibody or the antigen-binding fragment thereof blocks the inhibition of human ANGPTL3, mouse ANGPTL3, cynomolgus monkey ANGPTL3 and/or rat ANGPTL3 against LPL enzyme activity with an $IC_{50}$ value of less than 170 nM (e.g., less than or equal to 80 nM, less than or equal to 135 nM, or less than or equal to 55 nM). The $IC_{50}$ can be determined by the enzyme activity assay, e.g., as described in Test Example 3 of the present disclosure; and/or d. Exhibiting good lipid lowering effect. In some embodiments, the lipid lowering effect of the anti-ANGPTL3 antibody or the antigen-binding fragment thereof of the present disclosure is shown in Test Examples 5, 6 and/or 7. In some embodiments, the present disclosure provides a nucleic acid molecule encoding the anti-ANGPTL3 antibody or the antigen-binding fragment thereof described above.

In some embodiments, the present disclosure provides a vector comprising the nucleic acid molecule described above.

In some embodiments, the present disclosure provides a host cell comprising the nucleic acid molecule described above. In some embodiments, the present disclosure provides a host cell obtained by transformation (or transduction or transfection) with the vector described above; the host cell is selected from the group consisting of prokaryotic cells and eukaryotic cells, preferably eukaryotic cells, more preferably mammalian cells. In some embodiments, the host cell does not include any human cells capable of developing into a whole individual, such as human embryonic stem cells, fertilized eggs or germ cells; in some embodiments, the host cell is a eukaryotic cell, more preferably a mammalian cell including but not limited to CHO, 293, NSO, and a mammalian cell in which gene editing (e.g., knocking out genes such as FUT8 or GnT-III) can change the glycosylation modification of the antibody or the antigen-binding fragment thereof and thereby change the ADCC function of the antibody or the antigen-binding fragment thereof; in some embodiments, the mammalian cell does not include a human cell.

In some embodiments, the present disclosure provides a pharmaceutical composition comprising a therapeutically effective amount of the anti-ANGPTL3 antibody or the antigen-binding fragment thereof described above or the nucleic acid molecule described above, and one or more pharmaceutically acceptable carriers, diluents, buffers or excipients. In some embodiments, the pharmaceutical composition comprises, per unit dose, 0.01 wt. % to 99 wt. % of the anti-ANGPTL3 antibody or the antigen-binding fragment thereof described above or the nucleic acid molecule described above. In some embodiments, the pharmaceutical composition comprises, per unit dose, 0.1-2000 mg, more preferably 1-1000 mg, of the anti-ANGPTL3 antibody or the antigen-binding fragment thereof described above or the nucleic acid molecule described above.

In some embodiments, the present disclosure provides a method for immunodetection or determination of ANGPTL3, which comprises the anti-ANGPTL3 antibody or the antigen-binding fragment thereof described above. In another aspect, the present disclosure provides a method for detecting the expression level of ANGPTL3 in a sample from a subject in vitro, and the method comprises the step of contacting the anti-ANGPTL3 antibody or the antigen-binding fragment thereof described in the present disclosure with the sample; in some embodiments, the sample is a plasma, serum or whole blood sample from the subject. In some embodiments, the expression level of ANGPTL3 can be detected using any method known to those skilled in the art, including but not limited to Western blot, immunoblot, ELISA and mass spectrometry.

In some embodiments, the present disclosure provides a kit comprising the anti-ANGPTL3 antibody or the antigen-binding fragment thereof described above.

In some embodiments, the present disclosure provides a method for preparing the anti-ANGPTL3 antibody or the antigen-binding fragment thereof described above.

In some embodiments, the present disclosure provides use of the anti-ANGPTL3 antibody or the antigen-binding fragment thereof described above in preparing a reagent for immunodetection of ANGPTL3.

In some embodiments, the present disclosure provides the anti-ANGPTL3 antibody or the antigen-binding fragment thereof described above for use in immunodetection or determination of ANGPTL3.

In some embodiments, the present disclosure provides a kit comprising the anti-ANGPTL3 antibody or the antigen-binding fragment thereof described above. In some embodiments, the present disclosure provides a kit for detecting the expression level of ANGPTL3, which comprises the anti-ANGPTL3 antibody or the antigen-binding fragment thereof described above. In some embodiments, the kit is used in the method for detecting the expression level of ANGPTL3 described herein; in some embodiments, the detection method is any method known to those skilled in the art, including but not limited to Western blot, immunoblot, ELISA and mass spectrometry.

In some embodiments, the present disclosure provides a method for treating a disease or a disorder, which comprises administering to a subject a therapeutically effective amount of the anti-ANGPTL3 antibody or the antigen-binding fragment thereof, the nucleic acid molecule or the pharmaceutical composition described above; in some embodiments, the disease or the disorder is an ANGPTL3-associated disease or disorder; in some embodiments, the disease or the disorder is hypercholesterolemia, hyperlipidemia or an atherosclerotic disease.

In some embodiments, the present disclosure provides use of the anti-ANGPTL3 antibody or the antigen-binding fragment thereof, the nucleic acid molecule or the pharmaceutical composition described above in preparing a medicament for treating a disease or a disorder. In some embodiments, the disease or the disorder is an ANGPTL3-associated disease or disorder; in some embodiments, the disease or the disorder is hypercholesterolemia, hyperlipidemia or an atherosclerotic disease.

In some embodiments, the present disclosure provides the anti-ANGPTL3 antibody or the antigen-binding fragment thereof, the nucleic acid molecule or the pharmaceutical composition described above for use as a medicament. In some embodiments, the medicament is used for treating an ANGPTL3-associated disease or disorder; in some embodiments, the disease or the disorder is hypercholesterolemia, hyperlipidemia or an atherosclerotic disease.

DETAILED DESCRIPTION OF THE INVENTION

Terms (Definition)

In order to facilitate the understanding of the present disclosure, some technical and scientific terms are specifically defined below. Unless otherwise specifically defined herein, all other technical and scientific terms used herein have the meanings generally understood by those of ordinary skill in the art to which the present disclosure belongs.

The three-letter and single-letter codes for amino acids used in the present disclosure are as described in IUPAC- IUB Commission on Biochemical Nomenclature (CBN). A One-Letter Notation for Amino Acid Sequences. Tentative Rules. J. Biol. Chem., 1968, 243(13), 3557-3559.

The "antibody" described herein refers to an immunoglobulin, and a natural intact antibody is of a tetrapeptide chain structure formed by connection between two identical heavy chains and two identical light chains by interchain disulfide bonds. According to differences in the amino acid composition and the order of arrangement of the heavy chain constant regions, immunoglobulins can be divided into five classes, otherwise called isotypes of immunoglobulins, namely IgM, IgD, IgG, IgA and IgE, with their corresponding heavy chains being p chain, 6 chain, y chain, a chain and F chain, respectively. Ig of the same class can be divided into different subclasses according to differences in the amino acid composition of the hinge regions and the number and positions of disulfide bonds of the heavy chains; for example, IgG may be divided into IgG1, IgG2, IgG3 and IgG4. Light chains are classified into κ or λ chains by the differences in the constant regions. Each of the five classes of Ig may have a κ chain or λ chain.

In the heavy and light chains of antibodies, the sequences of about 110 amino acids near the N-terminal vary considerably and thus are referred to as variable regions (Fv regions); the remaining amino acid sequences near the C-terminal are relatively stable and thus are referred to as constant regions. The variable regions comprise 3 hypervariable regions (HVRs) and 4 framework regions (FRs) with relatively conservative sequences. The 3 hypervariable regions determine the specificity of the antibody and thus are also known as complementarity determining regions (CDRs). Each light chain variable region (VL) or heavy chain variable region (VH) consists of 3 CDRs and 4 FRs arranged from the amino-terminal to the carboxy-terminal in the following order: FR1, CDR1, FR2, CDR2, FR3, CDR3 and FR4. The 3 CDRs of the light chain refer to LCDR1, LCDR2 and LCDR3, and the 3 CDRs of the heavy chain refer to HCDR1, HCDR2 and HCDR3.

Besides full-length antibodies, the "antibodies" described herein also include antigen-binding fragments capable of binding to an antigen.

The antibodies described herein include human antibodies.

The "murine antibody" described herein is a monoclonal antibody against human ANGPTL3 prepared according to the knowledge and skill in the art. At the time of preparation, ANGPTL3 antigen is injected into test subjects, and then hybridomas expressing an antibody with the desired sequence or functional properties are isolated. In one preferred embodiment of the present disclosure, the murine anti-ANGPTL3 antibody or the antigen-binding fragment thereof may further comprise a light chain constant region of a murine κ or λ chain or a variant thereof, or further comprise a heavy chain constant region of a murine IgG1, IgG2, or IgG3 or a variant thereof.

The term "chimeric antibody" described herein refers to an antibody obtained by fusing a variable region of a heterologous (e.g., murine) antibody and a constant region of a parent antibody (e.g., human antibody), which can alleviate an immune response induced by the heterologous antibody. For example, the human-murine chimeric antibody is established by firstly establishing hybridoma secreting murine specific monoclonal antibody, then cloning a variable region gene from the mouse hybridoma cells, cloning a constant region gene of human antibody as required, connecting the mouse variable region gene and the human constant region gene into a chimeric gene, inserting the chimeric gene into an expression vector, and finally expressing chimeric antibody molecules in a eukaryotic system or prokaryotic system. In a preferred embodiment of the present disclosure, the antibody light chain of the anti-ANGPTL3 chimeric antibody further comprises a light chain constant region of a human κ or λ chain or a variant thereof. The antibody heavy chain of the ANGPTL3 chimeric antibody further comprises a heavy chain constant region of human IgG1, IgG2, IgG3 or IgG4 or a variant thereof, preferably a heavy chain constant region of human IgG1, IgG2 or IgG4, or an IgG1, IgG2 or IgG4 variant using an amino acid mutation (e.g., an L234A and/or L235A mutation, and/or an S228P mutation).

The term "humanized antibody", also referred to as CDR-grafted antibody, refers to an antibody produced by grafting mouse CDR sequences into a human antibody variable region framework, i.e., an antibody produced in a different type of human germline antibody framework sequence. Therefore, the heterogeneous reaction induced by the presence of a large number of mouse protein components in the chimeric antibody can be overcome. Such framework sequences can be obtained from public DNA databases or disclosed references that include germline antibody gene sequences. For example, germline DNA sequences of genes of the human heavy and light chain variable regions can be found in the "VBase" human germline sequence database, as well as in Kabat, E. A. et al., 1991 *Sequences of Proteins of Immunological Interest,* 5th edition. To avoid decreased activity caused by decreased immunogenicity, the variable region framework sequence of the human antibody may be subjected to a minimum reverse mutation or back mutation to retain activity. The humanized antibody of the present disclosure also include humanized antibodies which were further subjected to CDR affinity maturation mutation by yeast display.

The terms "human antibody" and "human-derived antibody" are used interchangeably and mean that one or more of the variable and constant regions are derived from human immunoglobulin sequences. One preferred way is that all of the variable and constant regions are derived from human immunoglobulin sequences, i.e., "fully human-derived antibodies" or "fully human antibodies". These antibodies can be obtained in a variety of ways, including antibodies obtained by isolating B cells from human PBMC, spleen and lymph node tissue and constructing natural single-stranded phage human antibody library by using phage display technology, or by immunizing transgenic mice capable of expressing human antibody light and heavy chains and screening. The human antibodies of the present disclosure also include antibodies that still bind to the antigen of interest and are obtained by mutation of one or more amino acids on the basis of human antibodies.

The "conventional variant" of the human antibody heavy chain constant region and the human antibody light chain constant region described herein refers to the variant of heavy chain constant region or light chain constant region derived from human that has been disclosed in the prior art and does not change the structure and function of the antibody variable region. Exemplary variants include IgG1, IgG2, IgG3 or IgG4 heavy chain constant region variants with site-directed modifications and amino acid substitutions in the heavy chain constant region. Specific substitutions are, for example, YTE mutation, L234A and/or L235A mutation, or S228P mutation, or mutations to obtain a knob-into-hole structure (so that the antibody heavy chain has a combination of knob-Fc and hole-Fc) known in the art.

These mutations have been confirmed to make the antibody have new properties, but do not change the function of the antibody variable region.

The terms "full-length antibody," "intact antibody," "complete antibody," and "whole antibody" are used interchangeably herein to refer to an antibody in its substantially intact form, as distinguished from an antigen-binding fragment defined below. The term especially refers to antibodies in which the light and heavy chains comprise constant regions. The "antibody" of the present disclosure include "full-length antibodies" and antigen-binding fragments thereof.

In some embodiments, the full-length antibodies of the present disclosure include full-length antibodies formed by linking a light chain variable region to a light chain constant region and linking a heavy chain variable region to a heavy chain constant region. Those skilled in the art can select different antibody-derived light chain constant regions and heavy chain constant regions according to actual needs, for example, human antibody-derived light chain constant regions and heavy chain constant regions.

The term "antigen-binding fragment" or "functional fragment" refers to one or more fragments of the antibody that retain the ability to specifically bind to an antigen (e.g., ANGPTL3). It has been shown that a fragment of a full-length antibody can be used to perform the antigen-binding function of the antibody. Examples of the binding fragment included in the term "antigen-binding fragment" include (i) Fab fragment, a monovalent fragment consisting of VL, VH, CL and CH1 domains; (ii) F(ab')2 fragment, a bivalent fragment comprising two Fab fragments linked by a disulfide bridge in the hinge region; (iii) Fd fragment, consisting of VH and CH1 domains; (iv) Fv fragment, consisting of VH and VL domains of one arm of the antibody; (V) dsFv, a stable antigen-binding fragment formed by VH and VL via interchain disulfide bonds therebetween; (vi) diabody, bispecific antibody and multi-specific antibody, comprising such fragments as scFv, dsFv and Fab. Furthermore, although the two domains of the Fv fragment, VL and VH, are encoded by separate genes, they can be linked by a synthetic linker by recombination, so that it is capable of producing a single protein chain in which the VL and VH regions pair to form a monovalent molecule (referred to as single-chain Fv (scFv); see, e.g., Bird et al. (1988) *Science* 242:423-426; and Huston et al. (1988) *Proc. Natl. Acad. Sci USA* 85:5879-5883). Such single-chain antibodies are also included in the term "antigen-binding fragment" of an antibody. Such antibody fragments are obtained using conventional techniques known to those skilled in the art, and screened for utility in the same manner as for intact antibodies. Antigen-binding portions may be produced using recombinant DNA technology or by enzymatic or chemical cleavage of intact immunoglobulins. Antibodies may be of different isotypes, e.g., IgG (e.g., subtype IgG1, IgG2, IgG3 or IgG4), IgA1, IgA2, IgD, IgE or IgM antibody.

Fab is an antibody fragment that has a molecular weight of about 50,000, has antigen-binding activity, and can be obtained by treating IgG antibody molecules with a protease papain (which cleaves the amino acid residue at position 224 of the H chain), in which about half of the H chain of the N-terminal side and the entire L chain are joined together by disulfide bonds.

F(ab')2 is an antibody fragment that has a molecular weight of about 100,000, has antigen-binding activity, comprises two Fab regions connected at the hinge position, and can be obtained by digesting the lower part of the two disulfide bonds in the hinge region of IgG with the enzyme pepsin.

Fab' is an antibody fragment that has a molecular weight of about 50,000, has antigen-binding activity, and can be obtained by cleaving the disulfide bond in the hinge region of the F(ab')2 described above. The Fab' of the present disclosure can be produced by using reducing agents, for example dithiothreitol, to treat the F(ab')2 of the present disclosure which specifically recognizes ANGPTL3 and binds to the amino acid sequence of the extracellular region or three-dimensional structure thereof.

In addition, the Fab' may be produced by inserting DNA encoding the Fab' fragment of an antibody into a prokaryotic or eukaryotic expression vector and introducing the vector into a prokaryote or a eukaryote to express the Fab'.

The term "single-chain antibody", "single-chain Fv" or "scFv" refers to a molecule comprising an antibody heavy chain variable domain (or region; VH) and an antibody light chain variable domain (or region; VL) linked by a linker. Such scFv molecules may have a general structure: NH2-VL-linker-VH-COOH or NH2-VH-linker-VL-COOH. Suitable linkers in the prior art consist of repeated GGGGS amino acid sequences or variants thereof, for example, 1-4 repeated variants (Holliger et al. (1993), *Proc. Natl. Acad. Sci. USA* 90:6444-6448). Other linkers that can be used in the present disclosure are described in Alfthan et al. (1995), *Protein Eng.* 8:725-731; Choi et al. (2001), *Eur. J. Immunol.* 31:94-106; Hu et al. (1996), *Cancer Res.* 56:3055-3061, Kipriyanov et al. (1999), *J. Mol. Biol.* 293:41-56; and Roovers R C, van der Linden E, de Bruine A P, Arends J W, Hoogenboom H R. In vitro characterisation of a monovalent and bivalent form of a fully human anti Ep-CAM phage antibody. Cancer Immunol Immunother, 2001, 50(2), 51-59.

A diabody is an antibody fragment in which scFv or Fab is dimerized, and is an antibody fragment with bivalent antigen-binding activity. In the bivalent antigen-binding activity, the two antigens can be identical or different.

Bispecific antibodies and multi-specific antibodies refer to the antibodies that can simultaneously bind to two or more antigens or antigenic determinants and comprise scFv or Fab fragments that can bind to ANGPTL3.

The diabody of the present disclosure can be produced by the following steps: obtaining the encoding cDNA of VH and VL of the monoclonal antibody of the present disclosure which specifically recognizes human ANGPTL3 and binds to the amino acid sequence of the extracellular region or a three-dimensional structure thereof, constructing the DNA encoding scFv so that the amino acid sequence length of the peptide linker is 8 residues or less, inserting the DNA into a prokaryotic expression vector or a eukaryotic expression vector, and then introducing the expression vector into a prokaryote or a eukaryote to express the diabody.

dsFv is obtained by linking polypeptides in which one amino acid residue in each VH and VL is substituted with a cysteine residue via disulfide bonds between the cysteine residues. The amino acid residues substituted with cysteine residues can be selected according to known methods (Reiter Y, Brinkmann U, Webber K O, Jung S H, Lee B, Pastan I. Engineering interchain disulfide bonds into conserved framework regions of Fv fragments: improved biochemical characteristics of recombinant immunotoxins containing disulfide-stabilized Fv. Protein Eng. 1994 May; 7(5):697-704 based on prediction of the three-dimensional structure of the antibody.

The full-length antibody or the antigen-binding fragment of the present disclosure can be produced by the following steps: obtaining the encoding cDNA the antibody of the present disclosure which specifically recognizes human ANGPTL3 and binds to the amino acid sequence of the extracellular region or a three-dimensional structure thereof, constructing the DNA encoding the dsFv, inserting the DNA into a prokaryotic expression vector or a eukaryotic expression vector, and then introducing the expression vector into a prokaryote or a eukaryote to express the dsFv.

The term "amino acid difference" or "amino acid mutation" refers to the presence of amino acid changes or mutations in the variant protein or polypeptide compared with the original protein or polypeptide, including occurrence of 1, 2, 3 or more amino acid insertions, deletions or substitutions on the basis of the original protein or polypeptide.

The term "antibody framework" or "FR" refers to a portion of a variable domain VL or VH, which serves as a framework for the antigen-binding loops (CDRs) of the variable domain. It is essentially a variable domain without CDRs.

The term "complementarity determining region," "CDR" or "hypervariable region" refers to one of the 6 hypervariable regions within the variable domain of an antibody which primarily contribute to antigen binding. In general, there are three CDRs (HCDR1, HCDR2 and HCDR3) in each heavy chain variable region and three CDRs (LCDR1, LCDR2 and LCDR3) in each light chain variable region. Any one of a variety of well-known schemes can be used to determine the amino acid sequence boundaries of the CDRs, including the "Kabat" numbering rules (see Kabat et al., (1991), "Sequences of Proteins of Immunological Interest", 5th edition, Public Health Service, National Institutes of Health, Bethesda, MD), "Chothia" numbering rules (see Al-Lazikani et al., (1997) JMB 273: 927-948) and ImMunoGenTics (IMGT) numbering rules (Lefranc M. P., Immunologist, 7, 132-136 (1999); Lefranc, M. P., et al., Dev. Comp. Immunol., 27, 55-77 (2003)), etc.

The term "epitope" or "antigenic determinant" refers to a site on an antigen (e.g., a specific site on an ANGPTL3 molecule) to which an immunoglobulin or an antibody specifically binds. Epitopes typically comprise at least 3, 4, 5, 6, 7, 8, 9, 10, 11, 12, 13, 14 or 15 contiguous or non-contiguous amino acids in a unique spatial conformation. See, e.g., Epitope Mapping Protocols in Methods in Molecular Biology, volume 66, G. E. Morris, Ed. (1996).

The terms "specific binding", "selective binding", "selectively bind to", "specifically bind to" and "capable of specifically binding to" refer to the binding of an antibody to an epitope on a predetermined antigen. In general, the antibody binds with an affinity (KD) of less than about $10^{-8}$ M, e.g., less than about $10^{-9}$ M, $10^{-10}$ M, or $10^{-11}$ M, $10^{-12}$ M or less.

The term "KD" refers to the dissociation equilibrium constant for specific antibody-antigen interaction. Generally, the antibody of the present disclosure binds to ANGPTL3 with a dissociation equilibrium constant (KD) of less than about $10^{-7}$ M, e.g., less than about $10^{-8}$ M or $10^{-9}$ M. For example, in the present disclosure, the affinity KD value of the antibody for the cell surface antigen is determined using the FACS method; in other embodiments, the affinity KD value of the antibody for the antigen is determined using the Biacore method; in other embodiments, binding of the antibody to the antigen is determined using the ELISA method.

The term "compete", when used in a case where antigen-binding proteins (e.g., neutralizing antigen-binding proteins or neutralizing antibodies) compete for the same epitope, refers to the competition between the antigen-binding proteins, which is determined by the following assays in which a test antigen-binding protein (e.g., an antibody or an immunologically functional fragment thereof) prevents or inhibits (e.g., reduces) specific binding of a reference antigen-binding protein (e.g., a ligand or a reference antibody) to a common antigen (e.g., ANGPTL3 antigen or a fragment thereof). Numerous types of competitive binding assays are available for determining whether an antigen-binding protein competes with another, such as: solid phase direct or indirect radioimmunoassay (RIA), solid phase direct or indirect enzyme immunoassay (EIA), and sandwich competition assay (see, e.g., Stahli et al., 1983, *Methods in Enzymology* 9:242-253); solid phase direct biotin-avidin EIA (see, e.g., Kirkland et al., 1986, *J. Immunol.* 137:3614-3619), solid phase direct labeled assay, and solid phase direct labeled sandwich assay (see, e.g., Harlow and Lane, 1988, *Antibodies: A Laboratory Manual*, Cold Spring Harbor Press); solid phase direct labeled RIA with I-125 label (see, e.g., Morel et al., 1988, *Molec. Immunol.* 25:7-15); solid phase direct biotin-avidin EIA (see, e.g., Cheung, et al., 1990, *Virology* 176:546-552) and direct labeled RIA (Moldenhauer et al., 1990, *Scand. J. Immunol.* 32:77-82). In general, the assay relates to a use of a purified antigen binding to a solid surface or a cell bearing any of an unlabeled assayed antigen-binding protein and a labeled reference antigen-binding protein. Competitive inhibition is measured by measuring the amount of label bound to the solid surface or the cell in the presence of the assayed antigen-binding protein. In general, the assayed antigen-binding protein is present in an excessive amount. Antigen-binding proteins identified by the competitive assay (competitive antigen-binding proteins) include: an antigen-binding protein binding to the same epitope as a reference antigen-binding protein, and an antigen-binding protein binding to an adjacent epitope sufficiently close to a binding epitope of the reference antigen-binding protein, and the two epitopes spatially interfere with each other to prevent the binding. Other detailed information regarding the method for assaying competitive binding is provided in the examples herein. In general, when the competitive antigen-binding protein exists in an excessive amount, the specific binding of the reference antigen-binding protein to the common antigen will be inhibited (such as reduced) by at least 40-45%, 45-50%, 50-55%, 55-60%, 60-65%, 65-70%, 70-75% or 75% or more. In some cases, the binding is inhibited by at least 80-85%, 85-90%, 90-95%, 95-97% or 97% or more.

The term "nucleic acid molecule" as used herein refers to a DNA molecule and an RNA molecule. The nucleic acid molecule may be single-stranded or double-stranded, and is preferably a double-stranded DNA, a single-stranded mRNA or a modified mRNA. A nucleic acid is "operably linked" when it is placed into a functional relationship with another nucleic acid sequence. For example, a promoter or enhancer is operably linked to a coding sequence if it affects the transcription of the coding sequence.

The amino acid sequence "identity" refers to the percentage of amino acid residues shared by a first sequence and a second sequence, wherein in aligning the amino acid sequences, gaps are introduced, when necessary, to achieve maximum percent sequence identity, and any conservative substitution is not considered as part of the sequence identity. For the purpose of determining percent amino acid sequence identity, alignments can be achieved in a variety of ways that are well-known in the art, for example, using publicly available computer software such as BLAST, BLAST-2, ALIGN, ALIGN-2 or Megalign (DNASTAR)

software. Those skilled in the art can determine parameters suitable for measuring alignment, including any algorithms required to achieve maximum alignment of the full length of the aligned sequences.

The term "expression vector" refers to a nucleic acid molecule capable of transporting another nucleic acid to which it has been linked. In one embodiment, the vector is a "plasmid" that refers to a circular double-stranded DNA loop into which additional DNA segments can be ligated. In another embodiment, the vector is a viral vector, wherein additional DNA segments may be ligated into the viral genome. The vectors disclosed herein are capable of autonomously replicating in a host cell into which they are introduced (e.g., bacterial vectors having a bacterial origin of replication and episomal mammalian vectors) or capable of integrating into the genome of a host cell after being introduced into the host cell and thus replicating with the host genome (e.g., non-episomal mammalian vectors).

Methods of producing and purifying antibodies and antigen-binding fragments are well known in the art, for example, those described in chapters 5-8 and 15 of *Antibodies: A Laboratory Manual*, Cold Spring Harbor Press. For example, mice can be immunized with human ANGPTL3 or a fragment thereof, and the obtained antibodies can be renatured and purified, and amino acid sequencing can be performed by using conventional methods. Antigen-binding fragments can likewise be prepared using conventional methods. The antibody or the antigen-binding fragment described in the present invention is genetically engineered to contain one or more additional human FRs in the non-human CDRs. Human FR germline sequences can be obtained at the website of ImMunoGeneTics (IMGT) by comparing the IMGT human antibody variable region germline gene database with the MOE software, or obtained from the Lefranc, M.-P., & Lefranc, G. (2001). *The immunoglobulin: factsbook.* Academic Press. ISBN: 012441351X.

The term "host cell" refers to a cell into which an expression vector has been introduced. Host cells may include bacterial, microbial, plant or animal cells. Bacteria susceptible to transformation include members of the Enterobacteriaceae family, such as strains of *Escherichia coli* or *Salmonella*; members of the Bacillaceae family, such as *Bacillus subtilis*; Pneumococcus; *Streptococcus* and *Haemophilus influenzae*. Suitable microorganisms include *Saccharomyces cerevisiae* and *Pichia pastoris*. Suitable animal host cell lines include CHO (Chinese hamster ovary cell line), 293 cells and NSO cells.

The engineered antibody or antigen-binding fragment of the present disclosure can be prepared and purified using conventional methods. For example, cDNA sequences encoding the heavy and light chains can be cloned and recombined into a GS expression vector. Recombinant immunoglobulin expression vectors can be stably transfected into CHO cells. As a more recommended prior art, mammalian expression systems will result in glycosylation of the antibody, particularly at the highly conservative N-terminal site of the Fc region. Stable clones are obtained by expression of the antibody that specifically binds to human ANGPTL3. Positive clones are expanded in serum-free medium in a bioreactor to produce the antibody. The culture solution with the secreted antibody can be purified using conventional techniques. For example, purification is carried out on an A or G Sepharose FF column containing an adjusted buffer. Non-specifically bound fractions are washed away. The bound antibody is eluted using pH gradient method, and the antibody fragments are detected using SDS-PAGE and collected. The antibody can be filtered and concentrated using conventional methods. Soluble mixtures and polymers can also be removed using conventional methods, such as molecular sieves and ion exchange. The resulting product needs to be immediately frozen, e.g., at −70° C., or lyophilized.

"Administrating" "giving" and "treating", when applied to animals, humans, experimental subjects, cells, tissues, organs or biological fluid, refer to contact of an exogenous drug, a therapeutic agent, a diagnostic agent or composition with the animals, humans, subjects, cells, tissues, organs or biological fluid. "Administrating" "giving" and "treating" can refer to, for example, therapeutic, pharmacokinetic, diagnostic, research and experimental methods. The treatment of the cells comprises contacting the reagent with the cells and contacting the reagent with fluid, wherein the fluid are in contact with the cells. "Administrating" "giving" and "treating" also refer to treating, e.g., cells by reagents, diagnosis, binding compositions or by another cell in vitro and ex vivo. "Treating", when applied to human, veterinary or research subjects, refers to therapeutic treatment, preventive or prophylactic measures, and research and diagnostic applications.

"Treating" or "treatment" refers to administering a therapeutic agent, such as a composition comprising any one of the conjugation compounds of the present disclosure, either internally or externally to a patient with one or more symptoms of a disease on which the therapeutic agent is known to have a therapeutic effect. Typically, the therapeutic agent is administered in an amount effective to alleviate one or more symptoms of the disease in the patient or population being treated to induce regression of such symptoms or inhibiting the development of such symptoms to any clinically measurable degree. The amount of therapeutic agent effective to alleviate the symptoms of any particular disease (also referred to as a "therapeutically effective amount") may vary depending on a variety of factors, such as the disease state, age, and weight of the patient, and the ability of the drug to produce a desired therapeutic effect in the patient. Whether a symptom of a disease has been alleviated can be evaluated by any clinical testing methods commonly used by doctors or other health care professionals to evaluate the severity or progression of the symptom. Although the embodiments of the present disclosure (for example treatment methods or products) may not be effective in alleviating all the target disease symptoms in every patient, as determined according to any statistical testing methods known in the art, such as Student t-test, chi-square test, Mann and Whitney's U test, Kruskal-Wallis test (H test), Jonckheere-Terpstra test and Wilcoxon test, they should reduce the target disease symptoms in a statistically significant number of patients.

"Conservative modification" or "conservative replacement or substitution" refers to replacement of amino acids in a protein with other amino acids having similar characteristics (e.g., charge, side-chain size, hydrophobicity/hydrophilicity, or backbone conformation and rigidity), so that changes can be frequently made without changing the biological activity of the protein. Those skilled in the art know that, generally speaking, a single amino acid replacement in a non-essential region of a polypeptide does not substantially change the biological activity (see, e.g., Watson et al. (1987) Molecular Biology of the Gene, The Benjamin/Cummings Pub. Co., p224, (4th edition)). In addition, the replacement of amino acids with similar structure or function is unlikely to disrupt the biological activity. Exemplary conservative substitutions are stated in the Table "Exemplary amino acid conservative substitutions" below.

TABLE 1

Exemplary amino acid conservative substitutions

| Original residue | Conservative substitution |
|---|---|
| Ala(A) | Gly; Ser |
| Arg(R) | Lys; His |
| Asn(N) | Gln; His; Asp |
| Asp(D) | Glu; Asn |
| Cys(C) | Ser; Ala; Val |
| Gln(Q) | Asn; Glu |
| Glu(E) | Asp; Gln |
| Gly(G) | Ala |
| His(H) | Asn; Gln |
| Ile(I) | Leu; Val |
| Leu(L) | Ile; Val |
| Lys(K) | Arg; His |
| Met(M) | Leu; Ile; Tyr |
| Phe(F) | Tyr; Met; Leu |
| Pro(P) | Ala |
| Ser(S) | Thr |
| Thr(T) | Ser |
| Trp(W) | Tyr; Phe |
| Tyr(Y) | Trp; Phe |
| Val(V) | Ile; Leu |

"Effective amount" or "effective dosage" refers to the amount of a drug, a compound or a pharmaceutical composition necessary to obtain any one or more beneficial or desired therapeutic results. For preventive use, the beneficial or desired results include elimination or reduction of risk, reduction of severity or delay of the onset of a disorder, including the biochemistry, histology and/or behavioral symptoms of the disorder, complications thereof and intermediate pathological phenotypes that appear during the progression of the disorder. For therapeutic applications, the beneficial or desired results include clinical results, such as reducing the incidence of various disorders related to the target antigen of the present disclosure or alleviating one or more symptoms of the disorder, reducing the dosage of other agents required to treat the disorder, enhancing the therapeutic effect of another agent, and/or delaying the progression of disorders of the patient related to the target antigen of the present disclosure.

"Exogenous" refers to substances produced outside organisms, cells or human bodies according to circumstances. "Endogenous" refers to substances produced inside cells, organisms or human bodies according to circumstances.

As used herein, the expressions "cell," "cell line," and "cell culture" are used interchangeably, and all such designations include their progenies. Therefore, the words "transformant" and "transformed cell" include primary test cells and cultures derived therefrom, regardless of the number of transfers. It should also be understood that all progenies may not be precisely identical in DNA content due to deliberate or unintentional mutations. Mutant progeny with the same function or biological activity as screened in the original transformed cells is included. When referring to different designations, they will become clear through the context.

"Polymerase chain reaction" or "PCR" as used herein refers to a procedure or technique in which a trace amount of a specific moiety of nucleic acid, RNA and/or DNA is amplified as described in, for example, U.S. Pat. No. 4,683,195. Generally speaking, it is necessary to obtain sequence information from the end or outside of the target region, so that oligonucleotide primers can be designed; these primers are the identical or similar in terms of sequence to the corresponding strand of the template to be amplified. The 5'-terminal nucleotide of 2 primers may coincide with the end of the material to be amplified. PCR can be used to amplify specific RNA sequences, specific DNA sequences from total genomic DNA and cDNA sequences transcribed from total cellular RNA, phage, plasmid sequences, or the like. See generally Mullis, et al., (1987) *Cold Spring Harbor Symp. Quant. Biol.* 51: 263; Ed. Erlich (1989) *PCR TECHNOLOGY* (Stockton Press, N.Y.). The PCR used herein is considered to be an example, but not the only one, of a nucleic acid polymerase reaction method for amplifying a nucleic acid test sample, and the method comprises using known nucleic acids as primers and nucleic acid polymerases to amplify or produce a specific moiety of the nucleic acid.

"Isolated" refers to a purified state, and in this case means that the designated molecule is substantially free of other biomolecules, such as nucleic acids, proteins, lipids, carbohydrates, or other materials (such as cell debris and growth medium). Generally, the term "isolated" does not mean the complete absence of such substances or the absence of water, buffers or salts, unless they are present in amounts that will significantly interfere with the experimental or therapeutic use of the compounds described herein.

The term "optional" or "optionally" means that the event or circumstance subsequently described may, but not necessarily, occur, and that the description includes instances where the event or circumstance occurs or does not occur.

The term "pharmaceutical composition" refers to a mixture containing one or more of the compounds described herein or physiologically/pharmaceutically acceptable salts or prodrugs thereof, and other chemical components, and the other components are, for example, physiologically/pharmaceutically acceptable carriers and excipients. The purpose of the pharmaceutical composition is to promote the administration to an organism, which facilitates the absorption of the active ingredient, thereby exerting biological activity.

The term "pharmaceutically acceptable carrier" refers to any inactive substance suitable for use in formulations for delivery of an antibody or an antigen-binding fragment. The carrier can be an anti-adhesive agent, binder, coating, disintegrant, filler or diluent, preservative (such as antioxidant, antibacterial or antifungal agent), sweetener, absorption delaying agent, wetting agent, emulsifier, buffer, etc. Examples of suitable pharmaceutically acceptable carriers include water, ethanol, polyol (such as glycerol, propanediol and polyethylene glycol), dextrose, vegetable oil (such as olive oil), saline, buffer, buffered saline, and isotonic agent such as sugar, polyol, sorbitol and sodium chloride.

In addition, the present disclosure includes agents for treating diseases related to positive cells of the target antigen (e.g., ANGPTL3), and the agents comprise the anti-ANGPTL3 antibody or the antigen-binding fragment thereof of the present disclosure as an active ingredient.

There is no limitation for the diseases related to ANGPTL3 in the present disclosure, as long as it is a disease related to ANGPTL3. For example, the therapeutic response induced by the molecule of the present disclosure can be achieved by binding to human ANGPTL3 and then blocking the binding of ANGPTL3 to its receptors. Thus, the molecules of the present disclosure, when in preparations and formulations suitable for therapeutic applications, are very useful for those suffering from hypercholesterolemia, hyperlipidemia, an atherosclerotic disease, or the like.

In addition, the present disclosure relates to methods for immunodetection or determination of the target antigen (e.g., ANGPTL3), reagents for immunodetection or determination of the target antigen (e.g., ANGPTL3), methods for immunodetection or determination of cells expressing the target antigen (e.g., ANGPTL3) and diagnostic agents for diagnosing diseases related to positive cells of the target antigen (e.g., ANGPTL3), which includes the antibody or the antibody fragment of the present disclosure as an active ingredient, which specifically recognizes the target antigen (e.g., human ANGPTL3) and binds to the amino acid sequence of the extracellular region or a three-dimensional structure thereof.

In the present disclosure, the method used for detection or determination of the amount of the target antigen (e.g., ANGPTL3) may be any known method. For example, it includes immunodetection or determination methods.

The immunodetection or determination methods are methods of detecting or determining the amount of antibody or antigen using labeled antigens or antibodies. Examples of immunodetection or determination methods include radioimmunoassay (RIA), enzyme immunoassay (EIA or ELISA), fluorescence immunoassay (FIA), luminescence immunoassay, western blotting, physicochemical methods, etc.

The aforementioned diseases related to positive cells of ANGPTL3 can be diagnosed by detecting or determining cells expressing ANGPTL3 by using the antibody or the antibody fragment of the present disclosure.

In order to detect cells expressing the polypeptide, known immunodetection methods can be used, preferably immunoprecipitation, fluorescent cell staining, immunohistochemical staining, etc. In addition, fluorescent antibody staining method utilizing the FMAT™ 8100 HTS (high-throughput screening) system (Applied Biosystem) can be used.

In the present disclosure, there is no particular limitation for the sample used for detection or determination of the target antigen (e.g., ANGPTL3), as long as it has the possibility of comprising cells expressing the target antigen (e.g., ANGPTL3), such as histocyte, blood, plasma, serum, pancreatic juice, urine, feces, tissue fluid or culture solution.

According to the required diagnostic method, the diagnostic agent containing the monoclonal antibody or the antibody fragment thereof of the present disclosure can also contain reagents for performing antigen-antibody reaction or reagents for detecting the reaction. The reagents for performing the antigen-antibody reaction include buffers, salts, etc. The reagents for detection include reagents commonly used in immunodetection or determination methods, for example labeled second antibodies that recognize the monoclonal antibody, the antibody fragment thereof or the conjugate thereof, and substrates corresponding to the label, etc.

One or more embodiments of the present invention are described in detail in the specification above. Although any methods and materials similar or identical to those described herein can also be used to implement or test the present invention, preferred methods and materials are described below. Other features, objects and advantages of the present invention will be apparent from the description and the claims. In the specification and claims, singular forms include plural referents unless otherwise indicated clearly in the context. Unless otherwise defined, all technical and scientific terms used herein have the meanings generally understood by those of ordinary skill in the art to which the present invention belongs. All the patents and publications cited in the specification are incorporated by reference. The following examples are set forth in order to more fully illustrate the preferred embodiments of the present invention. These examples should not be construed in any way as limiting the scope of the present invention, which is defined by the claims.

DETAILED DESCRIPTION

Figure 1:
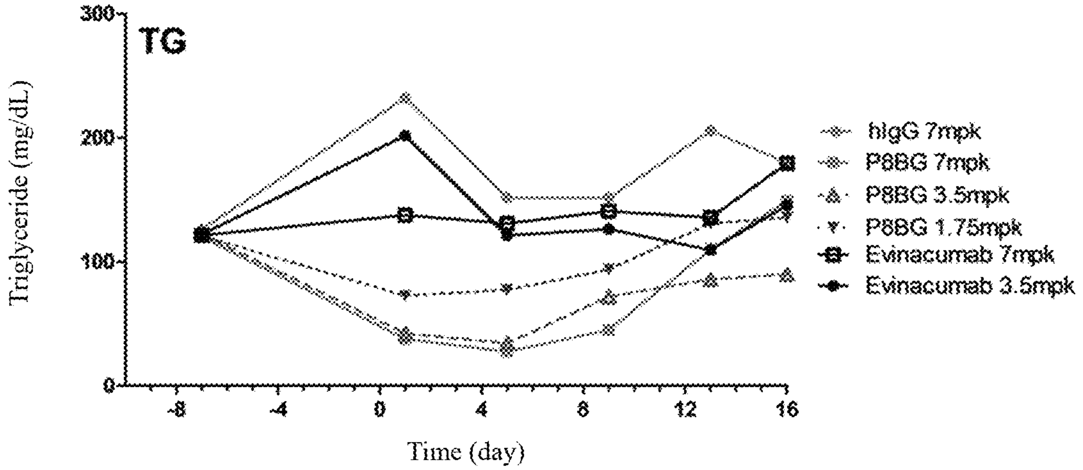
FIG. 1 shows the effect of the antibody P8BG on serum triglyceride of Sprague Dawley (SD) rats.

The following examples further illustrate the present disclosure, but the present disclosure is not limited thereto.

Experimental procedures without conditions specified in the Examples or Test Examples of the present disclosure are generally conducted according to conventional conditions, or according to conditions recommended by the manufacturer of the starting materials or commercial products. See Sambrook et al., Molecular Cloning: A Laboratory Manual, Cold Spring Harbor Laboratory; Ausubel et al., Current Protocols in Molecular Biology, Greene Publishing Associates and Wiley Interscience, NY. Reagents without specific origins indicated are commercially available conventional reagents.

EXAMPLES

Example 1: Design and Expression of ANGPTL3 Antigens

Human ANGPTL3 protein (Uniprot No.: Q9Y5C1), mouse ANGPTL3 protein (Uniprot No.: Q9R182), cynomolgus monkey ANGPTL3 protein (Uniprot No.: AOA2K5UDC5) and rat ANGPTL3 protein (Uniprot No.: F7FHP0) were used as templates of the ANGPTL3 of the present disclosure for designing antigens and proteins for detection related to the present disclosure. Different tags were fused to the ANGPTL3 proteins, and the obtained proteins were each subjected to cloning into a pTT5 vector (Biovector, Cat #: 102762), transient transfection expression in 293 cells and purification, thus obtaining the antigens and proteins for detection of the present disclosure.

1. Full-length human ANGPTL3: human-ANGPTL3(17-460)-His, used for immunization and detection and having the following amino acid sequence:

SEQ ID NO: 1

MEFGLSWLFLVAILKGVQCSRIDQDNSSFDSLSPEPKSRFAMLDDVKIL

ANGLLQLGHGLKDFVHKTKGQINDIFQKLNIFDQSFYDLSLQTSEIKEE

EKELRRTTYKLQVKNEEVKNMSLELNSKLESLLEEKILLQQKVKYLEEQ

LTNLIQNQPETPEHPEVTSLKTFVEKQDNSIKDLLQTVEDQYKQLNQQH

SQIKEIENQLRRTSIQEPTEISLSSKPRAPRTTPFLQLNEIRNVKHDGI

PAECTTIYNRGEHTSGMYAIRPSNSQVFHVYCDVISGSPWTLIQHRIDG

SQNFNETWENYKYGFGRLDGEFWLGLEKIYSIVKQSNYVLRIELEDWKD

NKHYIEYSFYLGNHETNYTLHLVAITGNVPNAIPENKDLVFSTWDHKAK

GHFNCPEGYSGGWWWHDECGENNLNGKYNKPRAKSKPERRRGLSWKSQN

GRLYSIKSTKMLIHPTDSESFE*HHHHHHHHHH*

Note: the single-underlined part represents signal peptide sequence, the italicized part represents the His sequence, and the bold part represents the amino acids of positions 17 to 460 of the full-length human ANGPTL3 protein.

2. Extracellular region of human ANGPTL3: human ANGPTL3(17-170)-Flag-His, used for immunization and detection and having the following amino acid sequence:

SEQ ID NO: 2

MEFGLSWLFLVAILKGVQCSRIDQDNSSFDSLSPEPKSRFAMLDDVKILAN

GLLQLGHGLKDFVHKTKGQINDIFQKLNIFDQSFYDLSLQTSEIKEEEKEL

RRTTYKLQVKNEEVKNMSLELNSKLESLLEEKILLQQKVKYLEEQLTNLI

QNQPETPEHPEVTSIKTFVEKGSS*DYKDDDDKHHHHHH*

Note: the single-underlined part represents the signal peptide, the double-underlined part represents the linker peptide, the italicized part represents the Flag and His, and the bold part represents the amino acids of positions 17 to 170 of the full-length human ANGPTL3 protein.

3. Fusion protein of the extracellular region of human ANGPTL3 (human ANGPTL3(17-170)) and the mouse IgG2aFc fragment (abbreviated as mFc): human ANGPTL3 (17-170)-mFc, used for detection and having the following amino acid sequence:

SEQ ID NO: 3

MEFGLSWLFLVAILKGVQCSRIDQDNSSFDSLSPEPKSRFAMLDDVKIL

ANGRRTTYKLQVKNEEVKNMSLELNSKLESLLEEKILLQQKVKYLEEQL

TNLIQNQPETPEHPEVTSLKTFVEK*EPRGPTIKPCPPCKCPAPNLLGGP*

*SVFIFPPKIKDVIMISLSPIVTCVVVDVSEDDPDVQISWFVNNVEVHTA*

*QTQTHREDYNSTLRVVSALPIQHQDWMSGKEFKCKVNNKDLPAPIERTI*

*SKPKGSVRAPQVYVLPPPEEEMTKKQVTLTCMVTDFMPEDIYVEWTNNG*

*KTELNYKNTEPVLDSDGSYFMYSKLRVEKKNWVERNSYSCSWHEGLHNH*

*HTTKSFSRTPGK*

Note: the underlined part represents the signal peptide, the italicized part represents the mouse IgG2aFc, and the bold part represents the amino acids of positions 17 to 170 of the full-length human ANGPTL3 protein.

4. Fusion protein of the extracellular region of human ANGPTL3 (human ANGPTL3(17-220)) and the mouse IgG2aFc fragment: human ANGPTL3(17-220)-mFc, which can be used for immunization and detection, and has the following amino acid sequence:

SEQ ID NO: 4

MEFGLSWLFLVAILKGVQCSRIDQDNSSFDSLSPEPKSRFAMLDDVKIL

ANGLLQLGHGLKDFVHKTKGQINDIFQKLNIFDQSFYDLSLQTSEIKEE

EKELRRTTYKLQVKNEEVKNMSLELNSKLESLLEEKILLQQKVKYLEEQ

LTNLIQNQPETPEHPEVTSLKTFVEKQDNSIKDLLQTVEDQYKQLNQQH

SQIKEIENQLRRTSIQEPTEISLSSKP*EPRGPTIKPCPPCKCPAPNLLG*

*GPSVFIFPPKIKDVLMISLSPIVTCVVVDVSEDDPDVQISWFVNNVEVH*

*TAQTQTHREDYNSTLRVVSALPIQHQDWMSGKEFKCKVNNKDLPAPIER*

*TISKPKGSVRAPOVYVLPPPEEEMTKKQVTLTCMVTDFMPEDIYVEWTN*

*NGKTELNYKNTEPVLDSDGSYFMYSKLRVEKKNWVERNSYSCSVVHEGL*

*HNHHTTKSFSRTPGK*

Note: the underlined part represents the signal peptide, the italicized part represents the mouse IgG2aFc, and the bold part represents the amino acids of positions 17 to 220 of the full-length human ANGPTL3 protein.

5. Full-length mouse ANGPTL3: mouse ANGPTL3(17-455)-His, used for immunization and detection and having the following amino acid sequence:

SEQ ID NO: 5

MEFGLSWLFLVAILKGVQCSRVDPDLSSFDSAPSEPKSRFAMLDDVKIL

ANGLLQLGHGLKDFVHKTKGQINDIFQKLNIFDQSFYDLSLRTNEIKEE

EKELRRTTSTLQVKNEEVKNMSVELNSKLESLLEEKTALQHKVRALEEQ

LTNLILSPAGAQEHPEVTSLKSFVEQQDNSIRELLQSVEEQYKQLSQQH

MQIKEIEKQLRKTGIQEPSENSLSSKSRAPRTTPPLQLNETENTEQDDL

PADCSAVYNRGEHTSGVYTIKPRNSQGFNVYCDTQSGSPWTLIQHRKDG

SQDFNETWENYEKGFGRLDGEFWLGLEKIYAIVQQSNYILRLELQDWKD

SKHYVEYSFHLGSHETNYTLHVAEIAGNIPGALPEHTDLMFSTWNHRAK

GQLYCPESYSGGWWWNDICGENNLNGKYNKPRTKSRPERRRGIYWRPQS

RKLYAIKSSKMMLQPTT*HHHHHHHHHH*

Note: the underlined part represents signal peptide, the italicized part represents the His sequence, and the bold part represents the amino acids of positions 17 to 455 of the full-length mouse ANGPTL3 protein.

6. Fusion protein of the extracellular region of mouse ANGPTL3 (mouse-ANGPTL3(17-220)) and mouse IgG2aFc segment: mouse ANGPTL3(17-220)-mFc, used for immunization and having the following amino acid sequence:

SEQ ID NO: 6

MEFGLSWLFLVAILKGVQCSRVDPDLSSFDSAPSEPKSRFAMLDDVKIL

ANGLLQLGHGLKDFVHKTKGQINDIFQKLNIFDQSFYDLSLRTNEIKEE

EKELRRTTSTLQVKNEEVKNMSVELNSKLESLLEEKTALQHKVRALEEQ

LTNLILSPAGAQEHPEVTSLKSFVEQQDNSIRELLQSVEEQYKQLSQQH

MQIKEIEKQLRKTGIQEPSENSLSSKS*EPRGPTIKPCPPCKCPAPNLLG*

-continued

*GPSVFIFPPKIKDVLMISLSPIVTCVVVDVSEDDPDVQISWFVNNVEVH*

*TAQTQTHREDYNSTLRVVSALPIQHQDWMSGKEFKCKVNNKDLPAPIER*

*TISKPKGSVRAPQVYVLPPPEEEMTKKQVTLTCMVTDFMPEDIYVEWTN*

*NGKTELNYKNTEPVLDSDGSYFMYSKLRVEKKNWVERNSYSCSWHEGLH*

*NHHTTKSFSRTPGK*

Note: the underlined part represents the signal peptide, the italicized part represents the mouse IgG2aFc, and the bold part represents the amino acids of positions 17 to 220 of the full-length mouse ANGPTL3 protein.

7. Full-length cynomolgus monkey ANGPTL3: cynomolgus monkey ANGPTL3(17-460)-His, used for detection and having the following amino acid sequence:

SEQ ID NO: 7

MEFGLSWLFLVAILKGVQCSRIDQDNSSFDSVSPEPKSRFAMLDDVKIL

ANGLLQLGHGLKDFVHKTKGQINDIFQKLNIFDQSFYDLSLQTSEIKEE

EKELRRTTYKLQVKNEEVKNMSLELNSKLESLLEEKILLQQKVKYLEEQ

LTNLIQNQPATPEHPEVTSLKSFVEKQDNSIKDLLQTVEEQYKQLNQQH

SQIKEIENQLRMTNIQEPTEISLSSKPRAPRTTPFLQLNEIRNVKHDGI

PADCTTIYNRGEHISGTYAIRPSNSQVFHVYCDVVSGSPWTLIQHRIDG

SQNFNETWENYKYGFGRLDGEFWLGLEKIYSIVKQSNYVLRIELEDWKD

NKHYIEYSFYLGNHETNYTLHVVKITGNVPNAIPENKDLVFSTWDHKAK

GHFSCPESYSGGWWWHDECGENNLNGKYNKPRTKSKPERRRGLSWKSQN

GRLYSIKSTKMLIHPTDSESFE*HHHHHHHHHH*

Note: the underlined part represents the signal peptide, the italicized part represents the His sequence, and the bold part represents the amino acids of positions 17 to 460 of the full-length cynomolgus monkey ANGPTL3 protein.

8. Full-length rat ANGPTL3: rat ANGPTL3(17-455)-His, used for detection and having the following amino acid sequence:

SEQ ID NO: 8

MEFGLSWLFLVAILKGVQCSRVDPDLSPFDSVPSEPKSRFAMLDDVKIL

ANGLLQLGHGLKDFVHKTKGQINDIFQKLNIFDQCFYDLSLQTNEIKEE

EKELRRTTSKLQVKNEEVKNMSLELNSKLESLLEEKMALQHRVRALEEQ

LTSLVQNPPGAREHPEVTSLKSFVEQQDNSIRELLQSVEEQYKQLSQQH

IQIKEIENQLRKTGIQEPTENSLYSKPRAPRTTPPLHLKEAKNIEQDDL

PADCSAIYNRGEHTSGVYTIRPSSSQVFNVYCDTQSGTPRTLIQHRKDG

SQNFNQTWENYEKGFGRLDGEFWLGLEKIYAIVKQSNYILRLELQDWKD

SKHYAEYSFHLGNHETNYTLHVAEIAANIPEALPEHRDLMFSTWDHRAK

GQLYCPESYSGGWWFSDMCGENNLNGKYNKPRAKSKPERRRGISWRPRG

GKLYSIKSSKMMLQPTT*HHHHHHHHHH*

Note: the underlined part represents the signal peptide, the italicized part represents the His sequence, and the bold part represents the amino acids of positions 17 to 455 of the full-length rat ANGPTL3 protein.

Example 2: Purification of ANGPTL3 Antigen Proteins, Hybridoma Antibodies and Recombinant Antibodies 1. Purification of Recombinant Proteins with His-Tag or Recombinant Proteins with Flag-His-Tag A cell expression sample was centrifuged at a high speed to remove cells and insoluble impurities, the supernatant was collected, and imidazole was added to reach a final concentration of 5 mM. A nickel column was equilibrated with a PBS solution containing 5 mM imidazole and washed with 2-5 column volumes. Cell supernatant was then loaded onto the column. The column was washed with PBS solution containing 5 mM imidazole until A280 reading dropped to baseline. The chromatography column was then washed with a mixture of PBS and 10 mM imidazole to remove non-specifically bound impure proteins, and the flow-through was collected. The target protein was eluted with PBS solution containing 300 mM imidazole and the elution peak was collected.

The collected eluate was further purified using a Superdex gel filtration column and then collected with tubes. The obtained sample was identified by SDS-PAGE, peptide map and LC-MS, and then aliquoted for later use if it was determined to be correct. Thus, the recombinant proteins with His tag or the recombinant proteins with Flag-His tag were obtained.

2. Purification of Hybridoma Antibodies or Recombinant Proteins with mFc Tag

A sample was centrifuged at a high speed to remove cells and insoluble impurities, and the supernatant was retained. A Protein A affinity column was equilibrated with 1×PBS and washed with 2-5 column volumes. The centrifuged cell expression supernatant sample was loaded onto the column. The column was washed with 1×PBS until $A_{280}$ reading dropped to baseline. The column was then washed with 1×PBS. The target protein was eluted with 0.1 M acetic acid (pH 3.5-4.0) and collected, and then the pH of the eluted protein was immediately adjusted to neutral with 1 M Tris-HCl (pH 7.0), and finally the eluted protein was subjected to dialysis or buffer exchange to 1×PBS buffer. The sample was collected, identified by electrophoresis, peptide map and LC-MS, and then aliquoted for later use if it was determined to be correct. Thus, the recombinant proteins with mFc tag or the hybridoma antibodies were obtained.

3. Purification of Antibodies and Recombinant Proteins with Fc Tag

A sample was centrifuged at a high speed to remove cells and insoluble impurities, and the supernatant was retained. A Protein G affinity column was equilibrated with 1×PBS and washed with 2-5 column volumes. The centrifuged cell expression supernatant sample was loaded onto the column. The column was washed with 1×PBS until $A_{280}$ reading dropped to baseline. The column was then washed with 1×PBS. The target protein was eluted with acetic acid (pH 3.0) and collected, and then the pH of the eluted protein was immediately adjusted to neutral with 1 M Tris-HCl (pH 7.0), and finally the eluted protein was subjected to dialysis or buffer exchange to 1×PBS buffer. The sample was collected, identified by electrophoresis, peptide map and LC-MS, and then aliquoted for later use if it was determined to be correct. Thus, the antibody or the recombinant protein with hFc tag was obtained.

Example 3: Preparation of Anti-ANGPTL3 Antibodies

1. Screening of Anti-ANGPTL3 Human-Derived Antibodies by Phage Library

A human phage single-chain antibody library was packaged and concentrated, and then the phage library ($10^{12}$-$10^{13}$/pfu) was suspended in 1 mL of 2% MPBS (PBS containing 2% of skim milk powder), and then 100 μL of Dynabeads® M-280 streptavidin (Invitrogen, Cat No. 11206D) was added. The tube was placed on a rotating plate and rolled over repeatedly, and then blocked at room temperature for 1 h. The tube was then placed on a magnetic rack for 2 min, the Dynabeads were removed, and then the phage library was transferred to a new tube. 2 μg/mL biotin-labeled human ANGPTL3(17-460)-His was added to the blocked phage library, and then the tube was placed on the rotating plate and rolled over repeatedly for 1 h. At the same time, 100 μL of Dynabeads was suspended in 1 mL of 2% MPBS, and then the tube was placed on a rotating plate and rolled over repeatedly, and then blocked at room temperature for 1 h. The tube was then placed on a magnetic rack for 2 min, and the blocking solution was pipetted off. The blocked Dynabeads were added to the mixture of the phage library and human ANGPTL3(17-460)-His, and the tube containing the resulting mixture was placed on a rotating plate and rolled over repeatedly for 15 min. The tube was then placed on a magnetic rack for 2 min, and the mixed solution was pipetted off. Dynabeads were washed 10 times with 1 mL of PBST (PBS containing 0.1% Tween-20), and 0.5 mL of 1 mg/mL trypsin (Sigma, Cat No. T1426-250MG) was added. The tube was then placed on a rotating plate and incubated for 15 min by rolling over repeatedly, and then elution was performed. The eluted phage was then used to infect *E. coli* TG1, which was then used for plating. Single clones were randomly picked for phage ELISA.

The clones were seeded into a 96-well deep-well plate (Nunc Cat No. 260251) and incubated at 37° C. for 16-18 h. A small number of the incubated clones were inoculated into another 96-well deep-well plate until the $OD_{600}$ reached about 0.5, and M13K07 helper phage (NEB, Cat No. N0315S) was then added for packaging. The mixture was centrifuged at 4000 g for 10 min to remove bacteria, and the culture solution was pipetted out for ELISA detection of ANGPTL3 binding. The positive clone strains were cryopreserved and sent to a sequencing company for sequencing. The amino acid sequences corresponding to the positive clones P3 and P8 are as follows:

> Heavy chain variable region sequence of P3:

SEQ ID NO: 9

QVQLVQSGAEVKKPGASVKVSCKSSGYTFTDYYLHWLRQAPGOGPEWMG
WISPNSGGTSYAQKFQGRVTMTRDTSISTAYMELSSLRSDDTAVYYCAR
DIATLGNFFTYGMDVWGQGTTVTVSS

-continued

> Light chain variable region sequence of P3:

SEQ ID NO: 10

DIQLTQSPSSLSASVGDRVTITCRASQGIRNDLGWYQQKPGKAPKLLIY
AASSLQSGVPSRFSGSGSGTDFTLTISSLQPEDFATYYCQQSYSSWTFG
QGTKVEIK

> Heavy chain variable region sequence of P8:

SEQ ID NO: 11

QVQLVQSGAEVKKPGASVKVSCKASGYTFTSYDINWVRQAPGQGLEWVG
LINPRDDSTSYAQKFQGRVTMTRDTSTSTMYMELSSLRSEDTAVYFCAR
DLGSIREVLYYGMDVWGQGTTVTVSS

> Light chain variable region sequence of P8:

SEQ ID NO: 12

DVVMTQSPLSLPVTPGEPASISCRSSQSLLHSNGYTYLDWYLQKPGQSP
QLLIYLGSNRASGVPDRFSGSGSGTDFTLKISRVEAEDVGVYYCMQALQ
TPLTFGQGTRLEIK

Note: the underlined parts in the sequences represent the CDR sequences determined according to the Kabat numbering system, and the italicized parts represent FR sequences.

2. Mutation of Anti-ANGPTL3 Antibody

Based on the three-dimensional structure of the P8 antibody, the amino acid residue at position 55 (naturally sequentially numbered) in the heavy chain variable region of P8 was mutated from D to E, and the amino acid residue at position 34 (naturally sequentially numbered) in the light chain variable region of P8 was mutated from G to V, thus obtaining a novel antibody molecule P8B, wherein the amino acid sequence of P8B is as follows:

>Heavy chain variable region sequence of P8B:

SEQ ID NO: 13

QVQLVQSGAEVKKPGASVKVSCKASGYTFTSYDINWVRQAPGQGLEWVG
LINPREDSTSYAQKFQGRVTMTRDTSTSTMYMELSSLRSEDTAVYFCAR
DLGSIREVLYYGMDVWGQGTTVTVSS

>Light chain variable region sequence of P8B:

SEQ ID NO: 14

DVVMTQSPLSLPVTPGEPASISCRSSQSLLHSNVYTYLDWYLQKPGQSP
QLLIYLGSNRASGVPDRFSGSGSGTDFTLKISRVEAEDVGVYYCMQALQ
YPLTFGQGTRLEIK

Note: the underlined parts in the sequences represent the CDR sequences determined according to the Kabat numbering system, and the italicized parts represent FR sequences.

TABLE 2

CDR sequences of anti-ANGPTL3 antibody molecules

| Antibody molecule | Light chain CDR | | Heavy chain CDR | |
|---|---|---|---|---|
| P3 | LCDR1 | RASQGIRNDLG (SEQ ID NO: 15) | HCDR1 | DYYLH (SEQ ID NO: 18) |
| | LCDR2 | AASSLQS (SEQ ID NO: 16) | HCDR2 | WISPNSGGTSYAQKFQG (SEQ ID NO: 19) |

TABLE 2-continued

CDR sequences of anti-ANGPTL3 antibody molecules

| Antibody molecule | | Light chain CDR | | Heavy chain CDR |
|---|---|---|---|---|
| | LCDR3 | QQSYSSWT (SEQ ID NO: 17) | HCDR3 | DIATLGNFFTYGMDV (SEQ ID NO: 20) |
| P8 | LCDR1 | RSSQSLLHSNGYTYLD (SEQ ID NO: 21) | HCDR1 | SYDIN (SEQ ID NO: 24) |
| | LCDR2 | LGSNRAS (SEQ ID NO: 22) | HCDR2 | LINPRDDSTSYAQKFQG (SEQ ID NO: 25) |
| | LCDR3 | MQALQTPLT (SEQ ID NO: 23) | HCDR3 | DLGSIREVLYYGMDV (SEQ ID NO: 26) |
| P8B | LCDR1 | RSSQSLLHSNVYTYLD (SEQ ID NO: 27) | HCDR1 | SYDIN (SEQ ID NO: 24) |
| | LCDR2 | LGSNRAS (SEQ ID NO: 22) | HCDR2 | LINPREDSTSYAQKFQG (SEQ ID NO: 28) |
| | LCDR3 | MQALQTPLT (SEQ ID NO: 23) | HCDR3 | DLGSIREVLYYGMDV (SEQ ID NO: 26) |

3. Construction and Expression of Anti-ANGPTL3 Antibodies

A primer was designed, and then a VH/VK gene fragment of the antibody was constructed by PCR and subjected to homologous recombination with an expression vector pHr (with a signal peptide and a constant region gene (CH1-FC/CL) fragment), thus constructing an expression vector VH-CH1-FC-pHr/VK-CL-pHr for a full-length antibody. The heavy chain constant region of the antibody may be selected from the group consisting of constant regions of human IgG1, IgG2, IgG4 and variants thereof, and the light chain constant region may be selected from the group consisting of the light chain constant regions of human κ and λ chains or variants thereof. Illustratively, the antibody heavy chain constant region is selected from the human IgG4-YTE variant having a sequence set forth in SEQ ID NO: 29, and the light chain constant region is selected from the constant region of human κ chain having a sequence set forth in SEQ ID NO: 30.

Illustratively, the light/heavy chain constant regions described above, together with the variable regions of P3, P8 and P8B described above, form complete anti-ANGPTL3 antibodies: P3G, P8G and P8BG, and the light/heavy chain sequences of the antibodies are as follows:

>Heavy chain sequence of P3G:

SEQ ID NO: 31

QVQLVQSGAEVKKPGASVKVSCKSSGYTFTDYYLHWLRQAPGQGPEWMGWI

SPNSGGTSYAQKFQGRVTMTRDTSISTAYMELSSLRSDDTAVYYCARDIAT

LGNFFTYGMDVWGQGTTVTVSSASTKGPSVFPLAPCSRSTSESTAALGCLV

KDYFPEPVTVSWNSGALTSGVHTFPAVLQSSGLYSLSSVVTVPSSSLGTKT

YTCNVDHKPSNTKVDKRVESKYGPPCPPCPAPEFLGGPSVFLFPPKPKDTL

YITREPEVTCVVVDVSQEDPEVQFNWYVDGVEVHNAKTKPREEQFNSTYRV

VSVLTVLHQDWLNGKEYKCKVSNKGLPSSIEKTISKAKGQPREPQVYTLPP

Heavy chain constant region sequence of human IgG4-YTE variant:

SEQ ID NO: 29

ASTKGPSVFPLAPCSRSTSESTAALGCLVKDYFPEPVTVSWNSGALTSGVHTF

PAVLQSSGLYSLSSVVTVPSSSLGTKTYTCNVDHKPSNTKVDKRVESKYGPPC

PPCPAPEFLGGPSVFLFPPKPKDTLYITREPEVTCVVVDVSQEDPEVQFNWYV

DGVEVHNAKTKPREEQFNSTYRVVSVLTVLHQDWLNGKEYKCKVSNKGLPS

SIEKTISKAKGQPREPQVYTLPPSQEEMTKNQVSLTCLVKGFYPSDIAVEWES

NGQPENNYKTTPPVLDSDGSFFLYSRLTVDKSRWQEGNVFSCSVMHEALHN

HYTQKSLSLSLGK

Light chain constant region sequence of human κ chain:

SEQ ID NO: 30

RTVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFNR

GEC

-continued

SQEEMTKNQVSLTCLVKGFYPSDIAVEWESNGQPENNYKTTPPVLDSDGSF

FLYSRLTVDKSRWQEGNVFSCSVMHEALHNHYTQKSLSLSLGK

>Light chain sequence of P3G:

SEQ ID NO: 32

DIQLTQSPSSLSASVGDRVTITCRASQGIRNDLGWYQQKPGKAPKLLIYAA

SSLQSGVPSRFSGSGSGTDFTLTISSLQPEDFATYYCQQSYSSWTFGQGTK

VEIKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPV

TKSFNRGEC

>Heavy chain sequence of P8G:

SEQ ID NO: 33

QVQLVGSGAEVKKPGASVKVSCKASGYTFTSYDINWVRQAPGQGLEWVGLI

NPRDDSTSYAQKFQGRVTMTRDTSTSTMYMELSSLRSEDTAVYFCARDLGS

IREVLYYGMDVWGQGTTVTVSSASTKGPSVFPLAPCSRSTSESTAALGCLV

KDYFPEPVTVSWNSGALTSGVHTFPAVLQSSGLYSLSSVVTVPSSSLGTKT

YTCNVDHKPSNTKVDKRVESKYGPPCPPCPAPEFLGGPSVFLFPPKPKDTL

YITREPEVTCVVVDVSQEDPEVQFNWYVDGVEVHNAKTKPREEQFNSTYRV

VSVLTVLHQDWLNGKEYKCKVSNKGLPSSIEKTISKAKGQPREPQVYTLPP

SQEEMTKNQVSLTCLVKGFYPSDIAVEWESNGQPENNYKTTPPVLDSDGSF

FLYSRLTVDKSRWQEGNVFSCSVMHEALHNHYTQKSLSLSLGK

>Light chain sequence of P8G:

SEQ ID NO: 34

DVVMTQSPLSLPVTPGEPASISCRSSQSLLHSNGYYYLDWYLQKPGQSPQL

LIYLGSNRASGVPDRFSGSGSGTDFTLKISRVEAEDVGVYYCMQALQTPLT

FGQGTRLEIKRTVAAPSVFIFPPSDEQLKSGTASVVCLLNNFYPREAKVQW

KVDNALQSGNSQESVTEQDSKDSTYSLSSTLTLSKADYEKHKVYACEVTHQ

GLSSPVTKSFNRGEC

>Heavy chain sequence of P8BG:

SEQ ID NO: 35

QVQLVQSGAEVKKPGASVKVSCKASGYTFTSYDINWVRQAPGQGLEWVGLI

NPREDSTSYAQKFQGRVTMTRDTSTSTMYMELSSLRSEDTAVYFCARDLGS

IREVLYYGMDVWGQGTTVTVSSASTKGPSVFPLAPCSRSTSESTAALGCLV

KDYFPEPVTVSWNSGALTSGVHTFPAVLQSSGLYSLSSVVTVPSSSLGTKT

YTCNVDHKPSNTKVDKRVESKYGPPCPPCPAPEFLGGPSVFLFPPKPKDTL

YITREPEVTCVVVDVSQEDPEVQFNWYVDGVEVHNAKTKPREEQFNSTYRV

VSVLTVLHQDWLNGKEYKCKVSNKGLPSSIEKTISKAKGQPREPQVYTLPP

SQEEMTKNQVSLTCLVKGFYPSDIAVEWESNGQPENNYKTTPPVLDSDGSF

FLYSRLTVDKSRWQEGNVFSCSVMHEALHNHYTQKSLSLSLGK

>Light chain sequence of P8BG:

SEQ ID NO: 36

DVVMTQSPLSLPVTPGEPASISCRSSQSLLHSNVYTYLDWYLQKPGQSPQL

LIYLGSNRASGVPDRFSGSGSGTDFTLKISRVEAEDVGVYYCMQALQTPLT

FGQGTRLEIKRTVAAPSVFIFPPSDEQLKSGTASVVCLLNNFYPREAKVQW

KVDNALQSGNSQESVTEQDSKDSTYSLSSTLTLSKADYEKHKVYACEVTHQ

GLSSPVTKSFNRGEC

Verification of Activity of the Antibodies of the Present Disclosure with Biochemical Test Methods

Test Example 1: ELISA Assay for Binding of Anti-ANGPTL3 Antibodies to ANGPTL3 Proteins An anti-ANGPTL3 antibody inhibited or interfered with at least one activity of an ANGPTL3 protein by binding to the ANGPTL3 protein. The binding activity of the anti-ANGPTL3 antibody to the ANGPTL3 antigen was tested by an ELISA assay. The ANGPTL3 protein (human ANGPTL3 (17-170)-mFc) was immobilized on a 96-well microplate by binding to the goat anti-mouse IgG coated on the microplate, and the binding activity of the antibody to the ANGPTL3 was determined according to the intensity of the signal after the antibody was added. Meanwhile, the ANGPTL3 proteins with a HIS tag (mouse ANGPTL3(17-455)-His, cynomolgus monkey ANGPTL3(17-460)-His and rat ANGPTL3(17-455)-His) labelled with a biotin labeling kit (Dojindo China, LK03) were immobilized on a 96-well microplate by binding to streptavidin coated on the microplate, and the binding activity of the antibody to the ANGPTL3 was determined according to the intensity of the signal after the antibody was added.

Goat anti-mouse IgG (Sigma, M3534-1ML) was diluted to a concentration of 2 μg/mL with PBS buffer (Shanghai BasalMedia, B320, pH 7.4), added to a 96-well microplate (Corning, CLS3590-100EA) at 50 μL/well, and then incubated in an incubator at 37° C. for 3 h or incubated at 4° C. overnight (16-18 h). After the liquid was discarded, a PBS-diluted 5% skim milk (BD, 232100) blocking solution was added at 250 μL/well, and the mixture was incubated in an incubator at 37° C. for 3 h or incubated at 4° C. overnight (16-18 h) for blocking. After the blocking was finished, the blocking solution was discarded and the plate was washed 3 times with PBST buffer (pH 7.4 PBS containing 0.05% Tween-20), and then human ANGPTL3(17-170)-mFc (with sequence set forth in SEQ ID NO: 3) diluted to 0.5 μg/mL with a sample diluent (pH 7.4 PBS containing 1% BSA) was added at 50 μL/well. The mixture was incubated in an incubator at 37° C. for 2 h. After the incubation was finished, the reaction solution in the microplate was discarded. The plate was washed 3 times with PBST, and then a test antibody that was diluted with a sample diluent to different concentrations was added at 50 μL/well. The mixture was incubated in an incubator at 37° C. for 2 h. After the incubation was finished, the plate was washed 3 times with PBST, and a goat anti-human secondary antibody (Jackson Immuno Research, 109-035-003) that was diluted with the sample diluent was added at 50 μL/well. The mixture was incubated at 37° C. for 1 h. The plate was washed 3 times with PBST, and then TMB chromogenic substrate (KPL, 52-00-03) was added at 50 μL/well. The mixture was incubated at room temperature for 2-5 min, and the reaction was terminated by adding 1 M $H_2SO_4$ at 50 μL/well. The absorbance at 450 nm was read using a VersaMax microplate reader, and the binding $EC_{50}$ value of the anti-ANGPTL3 antibody to ANGPTL3 antigen protein was calculated. The experimental results are shown in Table 3.

Streptavidin (Sigma, S4762-5MG) was diluted to a concentration of 3 μg/mL with PBS buffer (Shanghai BasalMedia, B320, pH 7.4), added to a 96-well microplate (Corning, CLS3590-100EA) at 50 μL/well, and then incubated in an incubator at 37° C. for 3 h or incubated at 4° C. overnight (16-18 h). After the liquid was discarded, a PBS-diluted 5% skim milk (BD, 232100) blocking solution was added at 250 μL/well, and the mixture was incubated in an incubator at 37° C. for 3 h or incubated at 4° C. overnight (16-18 h) for blocking. After the blocking was finished, the blocking solution was discarded and the plate was washed 3 times with PBST buffer (pH 7.4 PBS containing 0.05% Tween-20), and biotin-labeled mouse ANGPTL3(17-455)-His (with sequence set forth in SEQ ID NO: 5), cynomolgus monkey ANGPTL3(17-460)-His (with sequence set forth in SEQ ID NO: 7) and rat ANGPTL3(17-455)-His (with sequence set forth in SEQ ID NO: 8) each diluted to 0.5 μg/mL with a sample diluent (pH 7.4 PBS containing 1% BSA) was added at 50 μL/well. The mixture was incubated in an incubator at 37° C. for 2 h. After the incubation was finished, the reaction solution in the microplate was discarded. The plate was washed 3 times with PBST, and then a test antibody that was diluted with a sample diluent to different concentrations was added at 50 μL/well. The mixture was incubated in an incubator at 37° C. for 2 h. After the incubation was finished, the plate was washed 3 times with PBST, and an HRP-labeled goat anti-mouse secondary antibody (Jackson Immuno Research, 115-035-003), a goat anti-human secondary antibody (Jackson Immuno Research, 109-035-003) or a mouse HRP/anti-M13 conjugate secondary antibody (Sino Biological, Cat No. 11973-MM05-100, used for phage screening) diluted with a sample diluent was added at 50 μL/well. The mixture was incubated at 37° C. for 1 h. The plate was washed 3 times with PBST, and then TMB chromogenic substrate (KPL, 52-00-03) was added at 50 μL/well. The mixture was incubated at room temperature for 2-5 min, and the reaction was terminated by adding 1 M $H_2SO_4$ at 50 μL/well. The absorbance at 450 nm was read using a VersaMax microplate reader, and the binding $EC_{50}$ value of the anti-ANGPTL3 antibody to ANGPTL3 antigen protein was calculated. The experimental results are shown in Table 3. The results show that the anti-ANGPTL3 antibodies of the present disclosure are capable of binding to ANGPTL3 proteins of different species.

TABLE 3

ELISA assay for binding of anti-ANGPTL3 antibodies to ANGPTL3 proteins of different species

| Antibodies | Binding to human ANGPTL3 EC50 (nM) | Binding to mouse ANGPTL3 EC50 (nM) | Binding to cynomolgus monkey ANGPTL3 EC50(nM) | Binding to rat ANGPTL3 EC50 (nM) |
|---|---|---|---|---|
| P3G | 2.480 | 1.631 | 4.555 | 1.441 |
| P8G | 0.361 | 1.732 | 2.528 | 2.115 |
| P8BG | 0.172 | 0.105 | 0.200 | 0.528 |

Test Example 2: HTRF Assay for Binding of Anti-ANGPTL3 Antibodies to ANGPTL3 Antigen Proteins HTRF assay was also used to detect the binding activity of the anti-ANGPTL3 antibody to the antigen. The ANGPTL3 with a HIS tag (human ANGPTL3(17-460)-His, mouse ANGPTL3(17-455)-His, cynomolgus monkey ANGPTL3(17-460)-His and rat ANGPTL3(17-455)-His) labelled with a biotin labeling kit (Dojindo China, LK03) bound to the HTRF reagent Streptavidin-Tb cryptata (Cisbio, 610SATLA), and after the antibody was added, the antibody bound to the HTRF reagent Pab anti-mouse IgG-XL665 (Cisbio, 61PAMXLA) and angiopoietin-like protein 3. The intensity of the signal was used to determine the binding activity of the antibody to the angiopoietin-like protein 3.

4 μg/mL biotin-labeled human ANGPTL3(17-460)-His (with sequence set forth in SEQ ID NO: 1), mouse ANGPTL3(17-455)-His (with sequence set forth in SEQ ID NO: 5), cynomolgus monkey ANGPTL3(17-460)-His (with sequence set forth in SEQ ID NO: 7) and rat ANGPTL3 (17-455)-His (with sequence set forth in SEQ ID NO: 8) were each prepared using a diluent (pH 7.4 PBS containing 1% BSA) and added to a 384-well plate (PerkinElmer, optiplatte-384) at 5 μL/well, a mixed solution of the HTRF reagent Streptavidin-Tb cryptata and Pab anti-mouse IgG-XL665 was then added at 5 μL/well, and finally a test antibody that was diluted with a sample diluent to different concentrations was added at 10 μL/well. The mixture was incubated at 25° C. for 1 h. Values were read using a PHERAstar® FS microplate reader (BMG LabTECH) at the HTRF module, and the $EC_{50}$ value for binding of the anti-ANGPTL3 antibody to angiopoietin-like protein 3 was calculated. The experimental results are shown in Table 4. The results show that the antibodies of the present disclosure all have good binding activity for the ANGPTL3 antigens of human, mouse, cynomolgus monkey, rat and other species.

TABLE 4

HTRF assay for binding of anti-ANGPTL3 antibodies to ANGPTL3 proteins

| | $EC_{50}$ (nM) for binding to ANGPTL3 proteins | | | |
|---|---|---|---|---|
| Antibodies | Human ANGPTL3 | Mouse ANGPTL3 | Cynomolgus monkey ANGPTL3 | Rat ANGPTL3 |
| P3G | 0.929 | 0.638 | 0.502 | 0.597 |
| P8G | 0.784 | 0.450 | 0.303 | 0.484 |
| P8BG | 0.277 | 0.321 | 0.360 | 0.362 |

Test Example 3: Activity Assay for Blocking the Inhibition of LPL by Anti-ANGPTL3 Antibodies The enzyme activity detection experiment of LPL was used for detecting the activity of anti-ANGPTL3 antibody in blocking the inhibition of LPL enzyme by ANGPTL3 protein.

Bovine LPL (Sigma, L2254-5KU) was diluted with a dilution buffer (pH 7.4 PBS+2 mg/mL BSA) to 12.5 units and added to a 96-well plate (Corning, 3603) at 25 μL/well, then a test antibody that was diluted with a sample diluent to different concentrations was added at 25 μL/well., and then 27.6 μg/mL ANGPTL3 protein (human ANGPTL3(17-170) -Flag-His (with sequence set forth in SEQ ID NO: 2), mouse ANGPTL3(17-455)-His (with sequence set forth in SEQ ID NO: 5), cynomolgus monkey ANGPTL3(17-460)-His (with sequence set forth in SEQ ID NO: 7) and rat ANGPTL3(17-455)-His (with sequence set forth in SEQ ID NO: 8)) was added at 25 μL/well. The 96-well plate was shaken on a shaker for mixing the mixture well, which was then incubated in an incubator at 37° C. for 30 min. Finally, a 20 μM substrate (Sigma, 30058-10MG-F) diluted with a dilution buffer was added at 25 μL/well, and the 96-well plate was shaken on a shaker for mixing the mixture well, which was then incubated in an incubator at 37° C. for 30 min. The Ex535/Em612 was read using a FLEXSTATION™ 3 microplate reader. The concentrations and corresponding fluorescence data were processed using GRAPHPAD PRISM® 5 data analysis software, and the $IC_{50}$ was calculated. The experimental results are shown in Table 5. The results show that the antibodies of the present disclosure exhibit good blocking inhibition effect against LPL enzyme.

TABLE 5

Assay Results of activity of anti-ANGPTL3 antibodies in blocking inhibition of LPL by ANGPTL3 of different species

| | IC50(nM) | | | |
|---|---|---|---|---|
| Antibodies | Human ANGPTL3 | Mouse ANGPTL3 | Cyno ANGPTL3 | Rat ANGPTL3 |
| P3G | 68.9 | 167.5 | 42.4 | 66.5 |
| P8BG | 75.3 | 41.5 | 53.6 | 132.2 |

Test Example 4: Biacore Assay of Anti-ANGPTL3 Antibodies and ANGPTL3 Proteins

Biacore was used to determine the affinity of the test anti-ANGPTL3 antibodies for human, monkey, rat and mouse ANGPTL3, and the method is as follows:

A certain amount of test antibody was subjected to affinity capture by a Protein A biosensor chip (Cat. #29127556, GE), and then the human, monkey, rat and mouse ANGPTL3 antigens (human-ANGPTL3 (R&D, 3829-AN), mouse ANGPTL3(17-455)-His (with a sequence set forth in SEQ ID NO: 5), cynomolgus monkey ANGPTL3(17-460)-His (with a sequence set forth in SEQ ID NO: 7) and rat ANGPTL3(17-455)-His (with a sequence set forth in SEQ ID NO: 8)) at a certain concentration each flowed through the surface of the chip. Reaction signals were detected in real time using a Biacore T200 instrument to obtain association and dissociation curves. After each cycle of dissociation was completed, the biochip was washed and regenerated using a glycine-hydrochloric acid regeneration solution (Cat. #BR-1003-54, GE, pH 1.5). The running buffer for the experiment was 1×HBS-EP buffer (Cat. #BR-1001-88, GE). The data obtained from the experiment were fitted with the (1:1) Langmuir model using GE Biacore T200 evaluation software (version 3.0) to obtain affinity values. The experimental results are shown in Table 6. The results show that the anti-ANGPTL3 antibodies of the present disclosure are capable of binding to the human, cynomolgus monkey, rat and mouse ANGPTL3 antigens with high affinity.

TABLE 6

Results of Biacore assay of anti-ANGPTL3 antibodies and ANGPTL3 proteins

| Antibodies | Antigens | Association constant (1/Ms) | Dissociation constant (1/s) | Affinity (M) |
|---|---|---|---|---|
| P3G | Human ANGPTL3 | 2.56E+06 | 7.31E−04 | 2.85E−10 |
| | Cynomolgus monkey ANGPTL3 | 4.15E+06 | 8.47E−04 | 2.04E−10 |
| | Mouse ANGPTL3 | 9.81E+05 | 8.27E−04 | 8.43E−10 |
| | Rat ANGPTL3 | 1.28E+06 | 8.20E−04 | 6.39E−10 |
| P8G | Human ANGPTL3 | 2.20E+06 | 3.33E−04 | 1.51E−10 |
| | Cynomolgus monkey ANGPTL3 | 8.37E+06 | 4.97E−04 | 5.93E−11 |
| | Mouse ANGPTL3 | 9.70E+05 | 3.45E−04 | 3.55E−10 |
| | Rat ANGPTL3 | 1.34E+06 | 3.35E−04 | 2.50E−10 |
| P8BG | Human ANGPTL3 | 6.14E+06 | 2.76E−04 | 4.50E−11 |
| | Cynomolgus monkey ANGPTL3 | 5.18E+06 | 3.98E−04 | 7.69E−11 |

TABLE 6-continued

Results of Biacore assay of anti-ANGPTL3 antibodies and ANGPTL3 proteins

| Antibodies | Antigens | Association constant (1/Ms) | Dissociation constant (1/s) | Affinity (M) |
|---|---|---|---|---|
| | Mouse ANGPTL3 | 1.46E+06 | 4.20E−04 | 2.88E−10 |
| | Rat ANGPTL3 | 1.21E+06 | 3.11E−04 | 2.57E−10 |

Test Example 5: Evaluation of In Vivo Efficacy of Anti-ANGPTL3 Antibodies in Rats 1. In Vivo Lipid Lowering Experiment of Antibody P8BG in Rats SD rats for experiments (aged 4 weeks, SPF, about 100 g, male, purchased from Shanghai Slac Laboratory Animal Co., Ltd.; certification No.: 20170005013017, SCXK (Shanghai) 2017-0005) were subjected to 1 week of adaptive feeding in the laboratory environment (in a 12/12 hour light/dark cycle, at a temperature of 23±1° C. and a humidity of 40-50%), and the animals were fed with standard sterile mouse feed and had free access to food and water. 7 days before the start of the experiment, the animals were fasted for 4 h, and then blood was collected from the orbit and centrifuged at 3500 RPM for 15 min, and serum was collected. Serum lipid concentration (triglyceride) was determined using the ADVIA® 2400 clinical chemistry system (Siemens). The rats were divided into 6 groups by triglyceride level (non-relevant isotype human IgG protein (hIgG, the same below) as a negative control group, evinacumab (for sequence structure, see sequence of evinacumab in WHO Drug Information, Vol. 29, No. 3, 2015) 3.5 mpk group, evinacumab 7 mpk group, P8BG 3.5 mpk group, P8BG 1.75 mpk group, and P8BG 7 mpk group), 6 rats for each group. The rats in all the groups were each subjected to subcutaneous injection once, and then subjected to blood collection after 4 h of fasting on days 1, 5, 9, 13 and 16 after injection. Serum was separated out, and serum lipid concentration (triglyceride) was determined using the ADVIA® 2400 clinical chemistry system (Siemens). The experimental data were expressed as Mean±standard deviation (Mean±SEM) and plotted using GRAPHPAD PRISM® 5 data analysis software, and TTEST was used for statistical analysis.

The experimental results are shown in FIG. 1 and Table 7. Compared with the negative control group, 1 day after the administration, triglyceride in each treatment group was decreased, and statistical differences were observed in the groups except for the evinacumab 3.5 mpk group. During the experiment, triglyceride in the P8BG 7 mpk group was decreased by 83.7% at maximum, triglyceride in the P8BG 3.5 mpk group was decreased by 81.8% at maximum, and triglyceride in the P8BG 1.75 mpk group was decreased by 68.7% at maximum; 5 days after the administration, the decrease of triglyceride in the P8BG 3.5 mpk group, the P8BG 1.75 mpk group and the P8BG 7 mpk group still had statistical difference, while that in the evinacumab 3.5 mpk group and the evinacumab 7 mpk group had no statistical difference; 9 days after the administration, the decrease of triglyceride in the P8BG 7 mpk group and the P8BG 3.5 mpk group still had statistical difference. This indicates that P8BG has more effective and prolonged triglyceride lowering effect than evinacumab at the same dose. In addition, the animals in each group were normal in weight during the experiment.

TABLE 7

Effect of P8BG antibody on rat serum triglyceride

| | Antibodies | | | | |
|---|---|---|---|---|---|
| | Evinacumab | | P8BG | | |
| | Dosage for subcutaneous administration | | | | |
| | 7 mpk | 3.5 mpk | 7 mpk | 3.5 mpk | 1.75 mpk |
| Start TG (mg/dL) | 121.5 ± 17.0 | 122.2 ± 17.1 | 120.1 ± 14.3 | 122.6 ± 15.6 | 120.9 ± 16.1 |
| Minimum TG level | 131.1 ± 12.5 | 109.7 ± 16.7 | 27.6 ± 3.1 | 34.2 ± 4.7 | 72.6 ± 10.9 |
| Max Inh % | 40.7% | 13.1% | 83.7% | 81.8% | 68.7% |

Note:
Max Inh % refers to the maximum percentage of lipid lowering relative to the TG of the negative control group, and mpk refers to mg/kg.

2. In Vivo Lipid Lowering Experiment of Antibody P3G in Rats

SD rats for experiments (aged 4 weeks, SPF, male, purchased from Shanghai Slac Laboratory Animal Co., Ltd.; certification No.: 20170005013017, SCXK (Shanghai) 2017-0005) were subjected to 1 week of adaptive feeding in the laboratory environment (in a 12/12 hour light/dark cycle, at a temperature of 23±1° C. and a humidity of 40-50%), and the animals were provided with standard sterile mouse feed and had free access to food and water. 7 days before the start of the experiment, the animals were fasted for 4 h, and then blood was collected from the orbit and centrifuged at 3500 RPM for 15 min, and serum was collected. Serum lipid concentration (triglycerides) was determined using the ADVIA® 2400 clinical chemistry system (Siemens). The rats were divided into 4 groups by triglyceride level (hIgG negative control group, evinacumab 3.5 mpk group, P3G 3.5 mpk group and P3G 7 mpk group), 6 rats for each group. The rats in all the groups were each subjected to subcutaneous injection once, and then subjected to blood collection after 4 h of fasting on days 1, 5 and 9, 13 after injection. Serum was separated out, and serum lipid concentration (triglyceride) was determined using the ADVIA® 2400 clinical chemistry system (Siemens). The experimental data were expressed as Mean±standard deviation (Mean±SEM) and plotted using GRAPHPAD PRISM® 5 data analysis software, and TTEST was used for statistical analysis.

Figure 2:
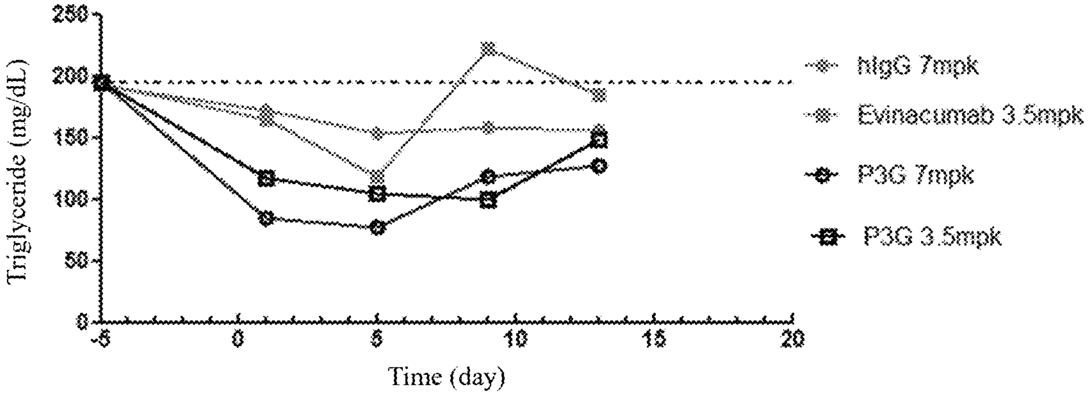
FIG. 2 shows the effect of antibody P3G on serum triglyceride of SD rats.

The experimental results are shown in FIG. 2. Compared with the hIgG negative control group, 1 day after the administration, triglyceride of each treatment group was decreased, and the degree of decrease of the P3G 3.5mpk group and the P3G 7 mpk group was greater than that of the evinacumab 3.5 mpk group; 9 days after the administration, serum lipid concentration of the P3G 3.5 mpk group and the P3G 7 mpk group remained lower than that of the positive control group.

Test Example 6: Determination of In Vivo Effect of Anti-ANGPTL3 Antibodies on Plasma Lipid Concentration in High-Fat High-Cholesterol Fed c57bl/6 Mice c57bl/6 mice (aged 4 weeks, SPF, about 16-18 g, male, purchased from Shanghai Cavens Laboratory Animal Co., Ltd.; certification No.: 201913812, SCXK (Jiangsu) 2016-0010) were subjected to 4 weeks of adaptive feeding (5 mice in each cage) in the laboratory environment (in a 12/12 hour light/dark cycle, at a temperature of 23±1° C. and a humidity of 40-50%), and the animals were fed with normal feed and had free access to food and water. 5 days after pre-blood collection, the common feed was changed to high-fat high-cholesterol feed (D12079B, purchased from Jiangsu Xietong Pharmaceutical Bio-engineering Co., Ltd.) for feeding the mice until the end of the experiment. 8 days before the start of the experiment, the animals were fasted for 4 h, and then blood was collected from the orbit and centrifuged at 8000 RPM for 2 min, and plasma was collected. Plasma lipid concentration was determined using the ADVIA® 2400 clinical chemistry system (Siemens). The mice were divided into 4 groups by triglyceride level (hIgG negative control group, evinacumab 25 mpk group, P8BG 25 mpk group and P8BG 5 mpk group), 11 mice for each group, and the mice were subjected to subcutaneous injection once a week, 8 times in total. At weeks 2, 3, 5, 7, 9, 10 and 11 after the start of the experiment, the mice in each group were fasted for 4 h, and then blood was collected from the orbit and plasma was collected. Plasma lipid concentration (triglyceride (TG), total cholesterol (TC) and LDL cholesterol (LDL-C)) were determined using the ADVIA® 2400 clinical chemistry system (Siemens). The experimental data were expressed as Mean±standard deviation (Mean±SEM) and plotted using GRAPHPAD PRISM® 5 data analysis software, and TTEST was used for statistical analysis.

Figure 3:
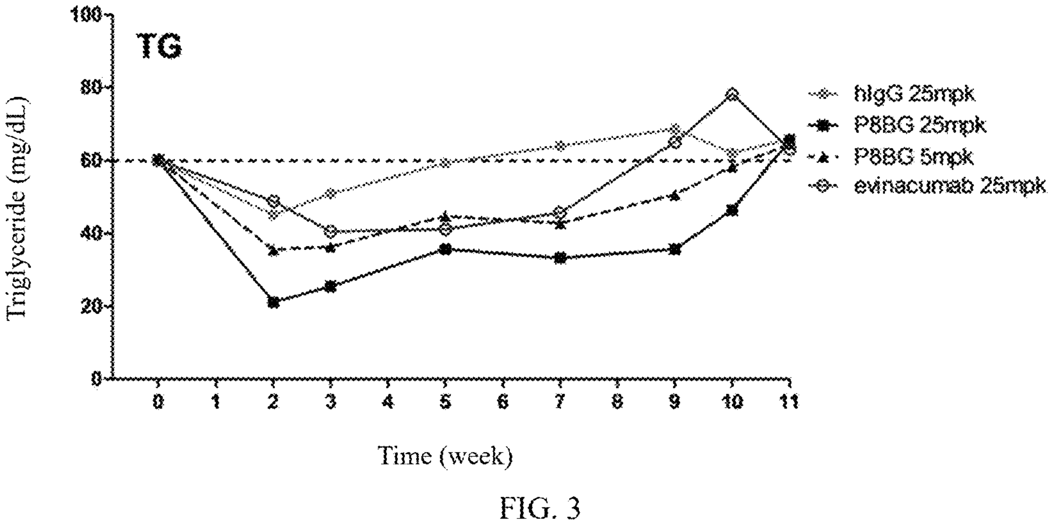
FIG. 3 shows the effect of anti-ANGPTL3 antibodies on plasma triglyceride of high-fat-diet (HFD) mice.
Figure 4:
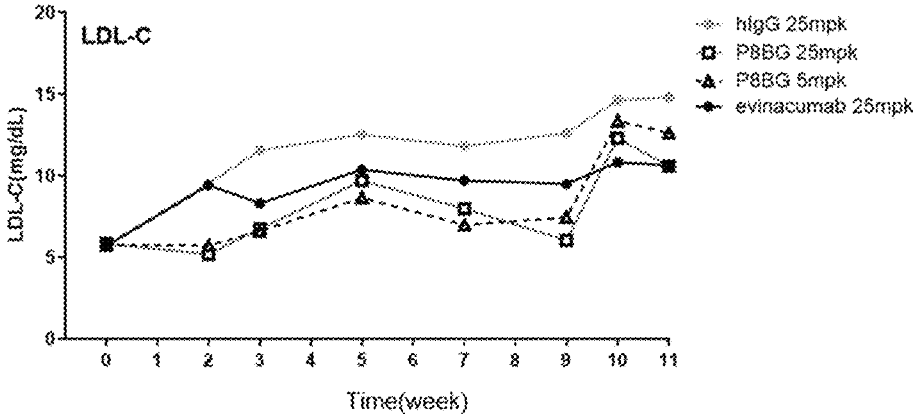
FIG. 4 shows the effect of anti-ANGPTL3 antibodies on plasma low-density lipoprotein cholesterol (LDL-C) of HFD mice.
Figure 5:
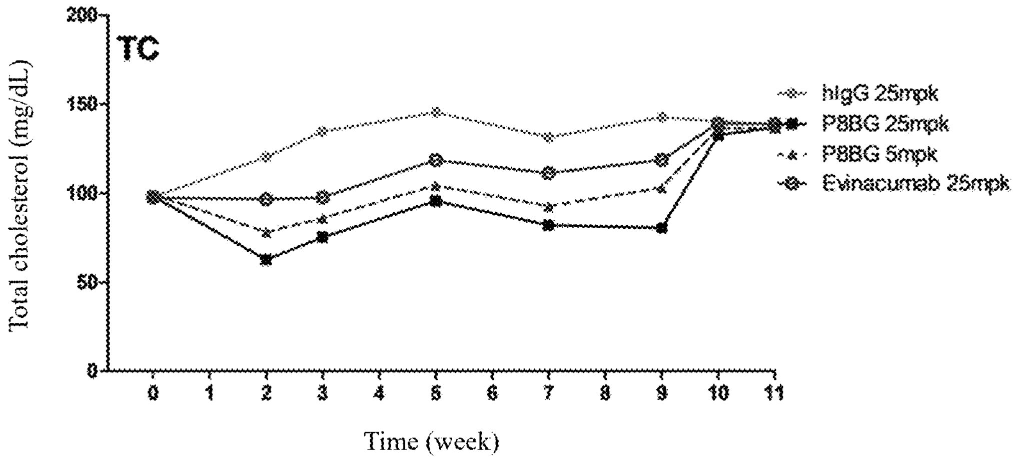
FIG. 5 shows the effect of anti-ANGPTL3 antibodies on plasma total cholesterol of HFD mice.

The results are shown in Tables 8-10 and FIGS. 3-5. Compared with the hIgG negative control group, the TG, TC and LDL-C were significantly decreased in the P8BG 25 mpk group 2, 3, 5 and 7 weeks after the start of the experiment; the evinacumab 25 mpk group and the P8BG 5 mpk group showed decrease in TG, TC and LDL-C 3, 5 and 7 weeks after the start of the experiment. 9 weeks after the start of the experiment, only two groups, the P8BG 25 mpk group and the P8BG 5 mpk group, showed significant decrease in triglyceride compared with the hIgG negative control group. Compared with the evinacumab 25 mpk group, the P8BG 25 mpk group showed significantly decreased triglyceride and total cholesterol on weeks 2, 3 and 9 of the experiment; compared with the evinacumab 25 mpk group, the P8BG 25 mpk group showed significantly decreased LDL-C on weeks 2 and 9 of the experiment. Throughout the entire experiment cycle from week 1 to week 11, the TG of the evinacumab 25 mpk group was decreased to as low as 40.5±2.3 at minimum, a 32.60% decrease compared with the start TG; and the TG of the P8BG 25 mpk group was decreased to as low as 21.1±1.3, a 64.90% decrease compared with the start TG. This indicates that the lipid lowering effect of the antibody P8BG is more effective and prolonged than that of evinacumab.

TABLE 8

Effect of anti-ANGPTL3 antibody on plasma TG in c57bl/6 mice

| | Antibodies | | | |
|---|---|---|---|---|
| | Evinacumab | P8BG | | hIgG |
| | Dosage for weekly subcutaneous administration | | | |
| | 25 mpk | 25 mpk | 5 mpk | 25 mpk |
| Start TG (mg/dL) | 60.1 ± 3.2 | 60.1 ± 4.1 | 60.1 ± 3.8 | 60.0 ± 6.2 |
| Minimum TG level | 40.5 ± 2.3 | 21.1 ± 1.3 | 35.5 ± 1.7 | 45.1 ± 7.1 |
| max Inh % | 32.6% | 64.9% | 40.9% | 24.8% |

Note:
max Inh % refers to the maximum percentage of lipid lowering relative to the start TG

TABLE 9

Effect of anti-ANGPTL3 antibodies on plasma LDL in c57bl/6 mice

| | Antibodies | | |
|---|---|---|---|
| | Evinacumab | P8BG | |
| | Dosage for weekly subcutaneous administration | | |
| | 25 mpk | 25 mpk | 5 mpk |
| Max Inh % | 28.10% | 52.10% | 42.80% |

Note:
Max Inh % refers to the maximum percentage of lipid lowering relative to the LDL of the negative control group

TABLE 10

Effect of anti-ANGPTL3 antibody on plasma TC in c57bl/6 mice

| | Antibodies | | |
|---|---|---|---|
| | Evinacumab | P8BG | |
| | Dosage for weekly subcutaneous administration | | |
| | 25 mpk | 25 mpk | 5 mpk |
| Max Inh % | 27.50% | 47.90% | 36.20% |

Note:
Max Inh % refers to the maximum percentage of lipid lowering relative to the TC of the negative control group

Test Example 7: Determination of In Vivo Effect of Anti-ANGPTL3 Antibodies on Plasma Lipid Concentration in APOE Mice APOE mice (aged 8 weeks, SPF, about 22 g, male, purchased from Shanghai Cavens Laboratory Animal Co., Ltd.; certification No.: 201917260, SCXK (Jiangsu) 2016-0010) were subjected to 4 weeks of adaptive feeding (2 mice in each cage) in the laboratory environment (in a 12/12 hour light/dark cycle, at a temperature of 23±1° C. and a humidity of 40-50%), and the animals were fed with high-fat feed (D12108C) and had free access to food and water. 7 days before the start of the experiment, the animals were fasted for 4 h, and then blood was collected from the orbit and centrifuged at 8000 RPM for 2 min, and plasma was collected. Plasma lipid concentration was determined using the ADVIA® 2400 clinical chemistry system (Siemens). Mice were divided into 5 groups by triglyceride level (hIgG negative control group, evinacumab 10 mpk group, evinacumab 5 mpk group, P8BG 10 mpk group and P8BG 5 mpk group), 8 mice for each group. The mice in all the groups were each subjected to subcutaneous injection once (see Table 11 for administration dosage for each group), and then subjected to blood collection from the orbit after 4 h of fasting on days 1, 7 and 11 after administration. Plasma was collected, and lipid concentrations (triglyceride and HDL cholesterol) were determined using the ADVIA® 2400 clinical chemistry system (Siemens). The experimental data were expressed as Mean±standard deviation (Mean±SEM) and plotted using GRAPHPAD PRISM® 5 data analysis software, and TTEST was used for statistical analysis.

Figure 6:
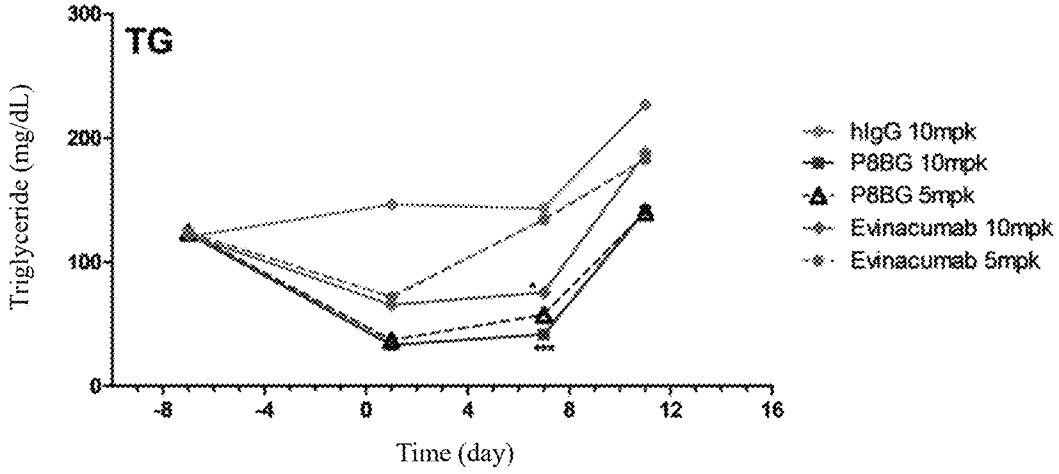
FIG. 6 shows the effect of anti-ANGPTL3 antibodies on plasma triglyceride of APOE mice (apolipoprotein E (ApoE) gene knockout mice)
Figure 7:
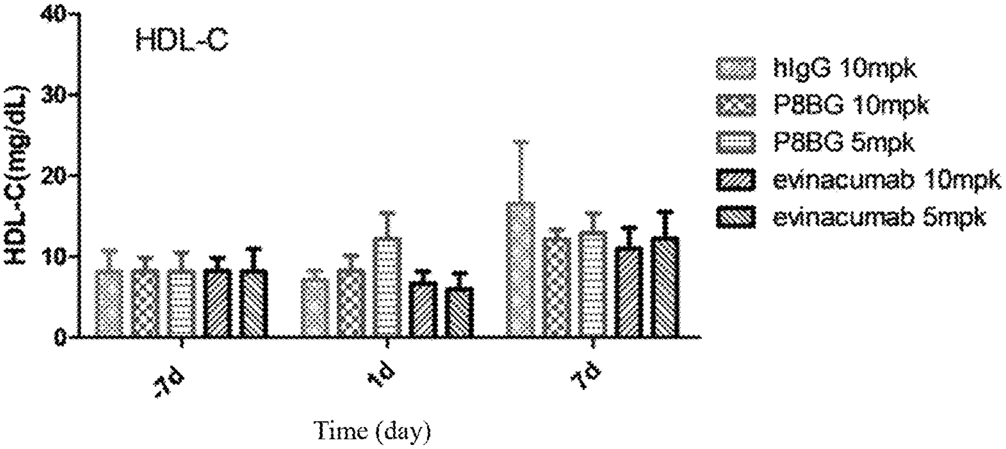
FIG. 7 shows the effect of anti-ANGPTL3 antibodies on plasma high-density liptein cholesterol (HDL-C) of APOE mice.

The experimental results are shown in FIGS. 6-7 and Table 11. Compared with the hIgG negative control group, 1 day after the administration, triglyceride in each treatment group was decreased. In the evinacumab (10 mpk) group, the triglyceride was decreased to as low as 65.6±5.4 mg/dL, a 46.2% decrease compared with the start TG value; in the evinacumab (5 mpk) group, the triglyceride was decreased to as low as 71.8±3.3 mg/dL, a 42.1% decrease compared with the start TG value; in the P8BG (10 mpk) group, the triglyceride was decreased to as low as 33.3±2.2 mg/dL, a 72.9% decrease compared with the start TG value; in the P8BG (5 mpk) group, the triglyceride was decreased to as low as 37.0±1.7 mg/dL, a 70.2% decrease compared with the start TG value. In addition, the experimental results show that 1 day after the administration, the plasma HDL-C of P8BG 10 mpk group was increased and the plasma HDL-C of evinacumab 10 mpk group was decreased. However, in the lipid lowering experiment, the decrease in the HDL-C is not generally desired during lipid lowering.

TABLE 11

Effect of anti-ANGPTL3 antibodies on plasma triglyceride in APOE mice

| | Antibodies | | | | |
|---|---|---|---|---|---|
| | Evinacumab | | P8BG | | hIgG |
| | Dosage for subcutaneous administration | | | | |
| | 10 mpk | 5 mpk | 10 mpk | 5 mpk | 10 mpk |
| Start TG (mg/dL) | 122.0 ± 8.8 | 123.9 ± 17.1 | 122.8 ± 10.7 | 124.0 ± 20.8 | 120.5 ± 14.9 |
| Minimum TG level | 65.6 ± 5.4 | 71.8 ± 3.3 | 33.3 ± 2.2 | 37.0 ± 1.7 | 146.7 ± 21.6 |
| max Inh % | 46.20% | 42.10% | 72.90% | 70.20% | −21.70% |

Note:
max Inh % refers to the maximum percentage of lipid lowering relative to the start TG

Test Example 8: Evaluation of Pharmacokinetics of Anti-ANGPTL3 Antibodies

In vivo pharmacokinetic experiment of anti-ANGPTL3 antibodies in mice C57BL/6 mice (18-24 g, purchased from Beijing Vital River Laboratory Animal Technology Co., Ltd.) were subjected to adaptive feeding (no less than 3 days) in the laboratory environment (in a 12/12 hour light/dark cycle, at a temperature of 16-26° C. and a humidity of 40-70%), and they had free access to food and water during the feeding. The day before the start of the experiment, the C57BL/6 mice were numbered and randomly grouped with 3 mice for each. On the day of experiment, mice in the groups were intravenously injected with test drugs P8BG and evinacumab, respectively, the administration dosage was 10 mg/kg, and the injection volume was 5 mL/kg.

The mice in the administration groups were each subjected to collection of 0.1 mL of whole blood before administration and 5 min, 8 h, 1 d, 2 d, 4 d, 7 d, 10 d, 14 d, 21 d and 28 d after the administration, and the blood was placed at 4° C. for 30 min without anticoagulation and then centrifuged at 1000 g for 15 min. The supernatant (serum) was collected, placed in an EP tube, and stored at −80° C.

Figure 8:
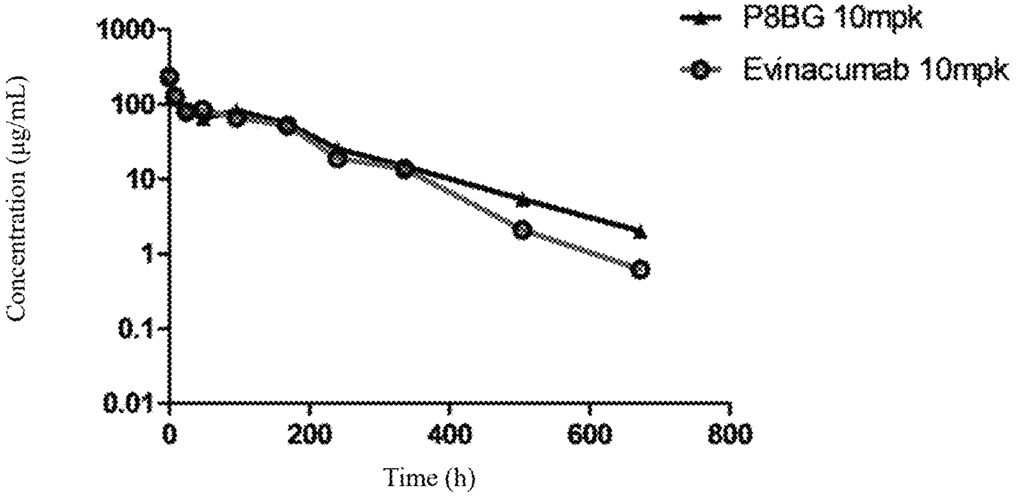
FIG. 8 shows the results of in vivo pharmacokinetic experiment of anti-ANGPTL3 antibodies in mice.

The antibody concentration in serum was determined by ELISA, and the pharmacokinetic parameters were calculated for the test drugs by Winnolin software. The main pharmacokinetic results obtained are shown in Table 12 and FIG. 8. The experimental results show that the P8BG antibody of the present disclosure has a higher half-life in mice than the positive control evinacumab.

2. Evaluation of Pharmacokinetics of Anti-ANGPTL3 Antibody in Cynomolgus Monkey

Cynomolgus monkeys (3-4 kg, purchased from Guangdong Qianyan Biological Science and Technology Co., Ltd.) were used, and the animals were subjected to at 14 days of quarantine and adaptive feeding before being used in the experiment. They were kept in stainless steel cages with no more than 2 animals per cage. The room temperature of the animal room was controlled to be 18-26° C., the relative humidity was 40-70%, and the illumination was in a 12/12 light/dark cycle. The animals had free access to water during the experiment. 6 cynomolgus monkeys were randomized into 2 groups with 3 animals per group according to biochemical criteria. The cynomolgus monkeys in the groups were subcutaneously injected with test drugs P8BG and evinacumab, respectively, the administration dosage was 10 mg/kg, and the injection volume was 2 mL/kg.

Figure 9:
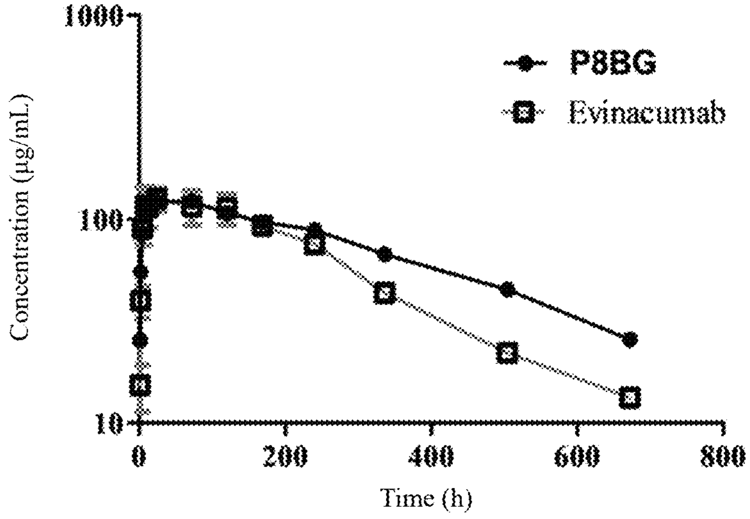
FIG. 9 shows the results of in vivo pharmacokinetic experiment of anti-ANGPTL3 antibodies in cynomolgus monkeys.

After the grouping, animals were fasted overnight, and they were each subjected to collection of about 2 mL of blood from veins of a lower limb before administration and 1 h, 2 h, 4 h, 8 h, 12 h, 1 d, 3 d, 5 d, 7 d, 10 d, 14 d, 21d, 28 d, 35 d, 42 d, 49 d and 56 d after administration. The blood was placed in a blood collection tube containing separation gel, left to stand at room temperature for 30 min and then centrifuged at 1000 g for 15 min. The supernatant was collected, aliquoted into 2 clean EP tubes and temporarily stored at −70° C. (completed within 2 h after blood collection). The antibody concentration in serum was determined by ELISA, and the pharmacokinetic parameters were calculated for the test drugs by Winnolin software. The main pharmacokinetic results obtained are shown in Table 14 and FIG. 9. The experimental results show that the antibody P8BG of the present disclosure has a higher half-life in cynomolgus monkeys than the positive control evinacumab.

TABLE 12

Pharmacokinetics of anti-ANGPTL3 antibodies in mice

| Antibodies | P8BG | Evinacumab |
|---|---|---|
| Route of administration | i.v. | i.v. |
| Administration dosage (mg/kg) | 10 | 10 |
| t½ h | 131.4 ± 18.8 | 71.1 ± 6.1 |
| t½ d | 5.47 ± 0.78 | 2.96 ± 0.25 |
| AUC0-∞(h*ug/ml) | 23272 ± 2887 | 16904 ± 4481 |

Note:
AUC0-∞: area under the plasma drug concentration-time curve; t½ (h): half-life (in hours); t½ (d): half-life (in days); i.v.: intravenous injection.

TABLE 13

Pharmacokinetics of anti-ANGPTL3 antibodies in cynomolgus monkeys

| | P8BG | Evinacumab |
|---|---|---|
| Administration dosage (mg/kg) | 10 | 10 |
| Route of administration | sc. | sc. |
| t½ h | 324.7 ± 115.3 | 157.7 ± 28.6 |
| t½ d | 13.5 ± 4.8 | 6.6 ± 1.2 |
| AUC0-∞ (ug/ml*h) | 44243 ± 7404 | 38027 ± 252 |

Note:
AUC0-∞: area under the plasma drug concentration-time curve; t½ (h): half-life (in hours); t½ (d): half-life (in days); sc.: subcutaneous injection. CLAIMS

The invention claimed is:

1. An anti-angiopoietin-like protein 3 (ANGPTL3) antibody or an antigen-binding fragment thereof, comprising a heavy chain variable region and a light chain variable region of an antibody, wherein:

i) the heavy chain variable region has a HCDR1, a HCDR2 and a HCDR3 identical to those of the heavy chain variable region set forth in SEQ ID NO: 13, and the light chain variable region has a LCDR1, a LCDR2 and a LCDR3 identical to those of the light chain variable region set forth in SEQ ID NO: 14; or ii) the heavy chain variable region has a HCDR1, a HCDR2 and a HCDR3 identical to those of the heavy chain variable region set forth in SEQ ID NO: 11, and the light chain variable region has a LCDR1, a LCDR2 and a LCDR3 identical to those of the light chain variable region set forth in SEQ ID NO: 12.

2. The anti-ANGPTL3 antibody or the antigen-binding fragment thereof according to claim 1, comprising a heavy chain variable region and a light chain variable region, wherein:

iv) the heavy chain variable region comprises a HCDR1, a HCDR2 and a HCDR3 having amino acid sequences set forth in SEQ ID NO: 24, SEQ ID NO: 28 and SEQ ID NO: 26, respectively, and the light chain variable region comprises a LCDR1, a LCDR2 and a LCDR3 having amino acid sequences set forth in SEQ ID NO: 27, SEQ ID NO: 22 and SEQ ID NO: 23, respectively; or v) the heavy chain variable region comprises a HCDR1, a HCDR2 and a HCDR3 having amino acid sequences set forth in SEQ ID NO: 24, SEQ ID NO: 25 and SEQ ID NO: 26, respectively, and the light chain variable region comprises a LCDR1, a LCDR2 and a LCDR3 having amino acid sequences set forth in SEQ ID NO: 21, SEQ ID NO: 22 and SEQ ID NO: 23, respectively.

3. The anti-ANGPTL3 antibody or the antigen-binding fragment thereof according to claim 1, comprising a heavy chain variable region and a light chain variable region, wherein:

(A) the heavy chain variable region has at least 90% sequence identity to SEQ ID NO: 13, and the light chain variable region has at least 90% sequence identity to SEQ ID NO: 14; or (B) the heavy chain variable region has at least 90% sequence identity to SEQ ID NO: 11, and the light chain variable region has at least 90% sequence identity to SEQ ID NO: 12.

4. The anti-ANGPTL3 antibody or the antigen-binding fragment thereof according to claim 3, comprising a heavy chain variable region and a light chain variable region, wherein:

(D) the heavy chain variable region comprises the amino acid sequence of SEQ ID NO: 13, and the light chain variable region comprises the amino acid sequence of SEQ ID NO: 14; or (E) the heavy chain variable region comprises the amino acid sequence of SEQ ID NO: 11, and the light chain variable region comprises the amino acid sequence of SEQ ID NO: 12.

5. The anti-ANGPTL3 antibody or the antigen-binding fragment thereof according to claim 1, wherein the anti-ANGPTL3 antibody further comprises a heavy chain constant region and a light chain constant region.

6. The anti-ANGPTL3 antibody or the antigen-binding fragment thereof according to claim 5, wherein the heavy chain constant region is selected from the group consisting of human IgG1, IgG2, IgG3 and IgG4 constant regions, and the light chain constant region is selected from the group consisting of human κ chain and λ chain constant regions.

7. The anti-ANGPTL3 antibody or the antigen-binding fragment thereof according to claim 5, wherein the heavy chain constant region has an amino acid sequence set forth in SEQ ID NO: 29 or an amino acid sequence having at least 85% sequence identity to SEQ ID NO: 29, and/or the light chain constant region has an amino acid sequence set forth in SEQ ID NO: 30 or an amino acid sequence having at least 85% sequence identity to SEQ ID NO: 30.

8. The anti-ANGPTL3 antibody or the antigen-binding fragment thereof according to claim 1, wherein the anti-ANGPTL3 antibody comprises a heavy chain and a light chain, wherein, (G) the heavy chain has at least 85% sequence identity to SEQ ID NO: 35, and the light chain has at least 85% sequence identity to SEQ ID NO: 36; or (H) the heavy chain has at least 85% sequence identity to SEQ ID NO: 33, and the light chain has at least 85% sequence identity to SEQ ID NO: 34.

9. The anti-ANGPTL3 antibody or the antigen-binding fragment thereof according to claim 1, wherein the anti-ANGPTL3 antibody comprises a heavy chain and a light chain, wherein:

(J) the heavy chain comprises the amino acid sequence as set forth in SEQ ID NO: 35, and the light chain comprises the amino acid sequence as set forth in SEQ ID NO: 36; or (K) the heavy chain comprises the amino acid sequence as set forth in SEQ ID NO: 33, and the light chain comprises the amino acid sequence as set forth in SEQ ID NO: 34.

10. A pharmaceutical composition, comprising:

(A) the anti-ANGPTL3 antibody or the antigen-binding fragment thereof according to claim 1, and (B) one or more pharmaceutically acceptable carriers, diluents, buffers or excipients.

11. A method for detecting the expression of ANGPTL3 in a sample, comprising the step of contacting the anti-ANGPTL3 antibody or the antigen-binding fragment thereof according to claim 1 with the sample, thereby determining the expression of ANGPTL3 in the sample.

12. A method for inhibiting the activity of ANGPTL3 in a subject in need thereof, the method comprising administering to the subject, a therapeutically effective amount of the anti-ANGPTL3 antibody or the antigen-binding fragment thereof according to claim 1 or the pharmaceutical composition according to claim 10, wherein the subject in need thereof has a disease or disorder is related to positive cells of ANGPTL3.

13. The method according to claim 12, wherein the disease or disorder is hypercholesterolemia, hyperlipidemia or an atherosclerotic disease.

* * * * *